(12) United States Patent
Frohberg

(10) Patent No.: US 7,449,623 B2
(45) Date of Patent: Nov. 11, 2008

(54) NUCLEIC ACID MOLECULES FROM RICE AND THEIR USE FOR THE PRODUCTION OF MODIFIED STARCH

(75) Inventor: Claus Frohberg, Berlin (DE)

(73) Assignee: Bayer Bioscience GmbH, Potsdam (DE)

( * ) Notice: Subject to any disclaimer, the term of this patent is extended or adjusted under 35 U.S.C. 154(b) by 130 days.

(21) Appl. No.: 10/327,288

(22) Filed: Dec. 20, 2002

(65) Prior Publication Data

US 2003/0145352 A1 Jul. 31, 2003

Related U.S. Application Data

(62) Division of application No. 09/436,874, filed on Nov. 9, 1999, now Pat. No. 6,521,816.

(60) Provisional application No. 60/107,883, filed on Nov. 9, 1998.

(51) Int. Cl.
*C12N 15/82* (2006.01)
*C12N 15/11* (2006.01)
*A01H 5/00* (2006.01)

(52) U.S. Cl. ............... 800/320.2; 536/24.5; 435/320.1; 435/419; 800/298; 800/285

(58) Field of Classification Search ............... 800/286, 800/284, 298, 320.3; 536/23.2, 23.6, 24.5; 435/320.1, 419; 424/93.2
See application file for complete search history.

(56) References Cited

U.S. PATENT DOCUMENTS 6,207,880 B1 3/2001 Kossmann et al.

FOREIGN PATENT DOCUMENTS

| WO | WO 92/11375 | 7/1992 |
|---|---|---|
| WO | WO 94/09144 | 4/1994 |
| WO | WO 95/07355 | 3/1995 |
| WO | WO 95/26407 | 10/1995 |
| WO | WO 98/27212 | 6/1998 |
| WO | WO 99/53072 | 10/1999 |

OTHER PUBLICATIONS

Colliver et al, 1997, Plant Mol. Biol. 35:509-522.*
Klann et al, 1996, Plant Physiol. 112:1321-1330.*
Tang et al, 1999, Plant Cell 11:177-189.*
van der Krol et al, 1990, Plant Mol. Biol. 14:457-466.*
Bird et al, 1991, Bio/Technol. 9:635-639.*
Kuipers et al, 1995, Mol. Gen. Genet. 246:745-755.*
Elkind, Y., et al., "Abnormal plant development and down-regulation of phenylpropanoid biosynthesis in transgenic tobacco containing a heterologous phenylalanine ammonia-lyase gene," Proc. Natl. Acad. Sci. USA, 87:9057-9061 (1990).
Faska, M., et al., Transgenic Tobacco Plants Expressing Pea Chloroplast *Nmdh* cDNA in Sense and Antisense Orientation, Plant Physiol., 115:705-715 (1997).
Bell, E., et al., A chroloplast lipoxygenase is required for wound-induced jasmonic acid accumulation in *Arabidopsis*, Proc. Natl. Acad. Sci. USA, 92:8675-8679 (1995).
Cheung, A.Y., et al., "A Floral Transmitting Tissue-Specific Glycoprotein Attracts Pollen Tubes and Stimulates Their Growth," 82:383-393 (1995).
Trevanion, S.J., et al., NADP-Malate Dehydrogenase in the $C_4$ Plant *Flaveria bidentis*, Plant Physiol. 113:1153-1165 (1997).
Bowie, J. U. et al., (1990) "Deciphering the Message in Protein Sequences: Tolerance to Amino Acid Substitutions." Science, vol. 247: 1306-1310.
Broun, P. et al., (1998) "Catalytic Plasticity of Fatty Acid Modification Enzymes Underlying Chemical Diversity of Plant Lipids." Science, vol. 282: 1315-1317.
Emmermann, M. and Kossmann, J. (Oct. 7, 1998) Accession No. W64232.
Itoh, K. et al., (1997) "Silencing of waxy genes in rice containing Wx transgenes." 1997, Mol Gen Genet, vol. 255: 351-358.
Konecki, D.S. et al., (1987) "The primary structure of human chromogranin A and pancreastatin," J. Biol. Chem. 262: 17026-17030.
Kossmann, J. et al., (1995) "Transgenic plants as a tool to understand starch biosynthesis." Progress in Biotechnol., vol. 10: 271-278.
Lazar, E. et al., (1988) "Transforming Growth Factor a: Mutation of Aspartic Acid 47 and Leucine 48 Results in Different Biological Activities." Molecular and Cellular Biology, vol. 8: 1247-1252.
Sonnewald, U. et al., (1995) "A second L-type isozyme of potato glucan phosphorylase: cloning, antisense inhibition and expression analysis." Plant Molecular Biology, vol. 27: 567-576.

* cited by examiner

*Primary Examiner*—Anne R Kubelik
(74) *Attorney, Agent, or Firm*—Hunton & Williams LLP

(57) ABSTRACT

Nucleic acid molecules are described encoding a starch granule-bound protein from rice as well as methods and recombinant DNA molecules for the production of transgenic plant cells and plants synthesizing a modified starch. Moreover, the plant cells and plants resulting from those methods as well as the starch obtainable therefrom are described.

20 Claims, 1 Drawing Sheet

Figure 1:
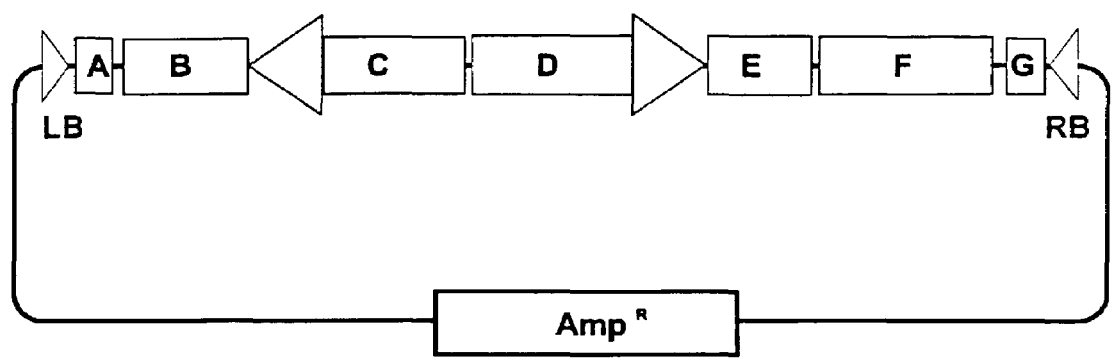

NUCLEIC ACID MOLECULES FROM RICE AND THEIR USE FOR THE PRODUCTION OF MODIFIED STARCH

This application is a divisional of U.S. application Ser. No. 09/436,874, filed Nov. 9, 1999, which claims the benefit of U.S. Patent Application No. 60/107,883, filed Nov. 9, 1998.

The present invention relates to nucleic acid molecules encoding an R1-protein from rice as well as to methods and recombinant DNA molecules for the production of transgenic plant cells and plants synthesizing modified starch. The invention also relates to the transgenic plant cells and plants resulting from these methods and to the starch obtainable from the transgenic plant cells and plants.

The polysaccharide starch, which constitutes one of the most important storage substances in plants, is not only used in the area of foodstuffs but also plays a significant role as a regenerative material in the manufacturing of industrial products. In order to enable the use of this raw material in as many areas as possible, it is necessary to obtain a large variety of substances as well as to adapt these substances to the varying demands of the processing industry.

Although starch consists of a chemically homogeneous basic component, namely glucose, it does not constitute a homogeneous raw material. It is rather a complex mixture of various types of molecules which differ from each other in their degree of polymerization and in the degree of branching of the glucose chains. One differentiates particularly between amylose-starch, a basically non-branched polymer made up of α-1,4-glycosidically branched glucose molecules, and amylopectin-starch which in turn is a mixture of more or less heavily branched glucose chains. The branching results from the occurrence of α-1,6-glycosidic interlinkings.

The molecular structure of starch which is mainly determined by its degree of branching, the amylose/amylopectin ration, the average chain-length and the occurrence of phosphate groups is significant for important functional properties of starch or, respectively, its watery solutions. Important functional properties are for example solubility of the starch, tendency to retrogradation, capability of film formation, viscosity, pastification properties, i.e. binding and gluing properties, as well as cold resistance. The starch granule size may also be significant for the various uses. The production of starch with a high amylose content is particularly significant. Furthermore, modified starch contained in plant cells may, under certain conditions, favorably alter the behavior of the plant cell. For example, it would be possible to decrease the starch degradation during the storage of the starch-containing organs such as seeds and tubers prior to their further processing by, for example, starch extraction. Moreover, there is some interest in producing modified starches which would render plant cells and plant organs containing this starch more suitable for further processing, such as for the production of popcorn or corn flakes from maize or of French fries, crisps or potato powder from potatoes. There is a particular interest in improving the starches in such a way, that they show a reduced "cold sweetening", i.e. a decreased release of reduced sugars (especially glucose) during long-term storage at low temperatures.

Furthermore, in the case of rice, it is known that the change of the starch's physico-chemical properties influences the cooking and eating qualities of rice grains. The possibility of altering and fine-tuning these properties would permit the development of new rice varieties with a specific quality type. Quality types are usually based on the starch properties or textures of cooked rice, specifically apparent amylose content (AC), final starch gelatinization temperature (GT), and gel consistency (GC) of milled rice (Juliano, *Cereal Foods World* 43 (1998), 207-222).

Starch which can be isolated from plants is often adapted to certain industrial purposes by means of chemical modifications which are usually time-consuming and expensive. Therefore it is desirable to find possibilities to produce plants synthesizing a starch the properties of which already meet the demands of the processing industry.

Conventional methods for producing such plants are classical breeding methods and the production of mutants both of which are, however, expensive and time consuming. Alternatively, plants synthesizing starch with altered properties may be produced by means of recombinant DNA techniques. However, in order to make use of recombinant DNA techniques, DNA sequences are required the gene products of which influence starch synthesis, starch modification or starch degradation, in particular sequences of such an important starch-synthesizing plant as rice.

Therefore, the problem underlying the present invention is to provide nucleic acid molecules and methods which allow for the alteration of plants in such a way, that they synthesize a starch which differs from starch naturally synthesized in plants with respect to its physical and/or chemical properties (these properties in turn influence, for example, the cooking properties and/or the nutritional value of the harvestable parts of these plants) and which starch is therefore more suitable for general and/or particular uses.

This problem is solved by the provision of the embodiments described in the claims.

Therefore, the present invention relates to nucleic acid molecules encoding a protein, in particular from rice, comprising the amino acid sequence indicated in Seq. ID No. 2. Such proteins are present in the plastids of plant cells, particularly in the plastids of cells from rice. In the scope of the present invention the protein encoded by the described nucleic acid molecules is referred to as an R1-protein. It is suspected that this protein exists in the plastids in a form bound to the starch granules as well as in a soluble form. Furthermore, this protein is involved in the phosphorylation of starch.

The present invention further relates to nucleic acid molecules comprising the nucleotide sequence indicated in Seq. ID No. 1, particularly the coding region indicated in Seq. ID No. 1.

The present invention also relates to nucleic acid molecules encoding a polypeptide comprising the amino acid sequence as encoded by the cDNA insert of plasmid DSM 12439.

Furthermore, the present invention relates to nucleic acid molecules comprising the coding region contained in the cDNA insert of plasmid DSM 12439.

Nucleic acid molecules encoding a protein in particular from rice, which occurs in the plastids of the cells, and hybridizing to the above-mentioned nucleic acid molecules of the invention or their complementary strand are also the subject matter of the present invention. In this context the term "hybridization" signifies hybridization under conventional hybridizing conditions, preferably under stringent conditions as described for example in Sambrook et al., *Molecular Cloning, A Laboratory Manual*, 2$^{nd}$ Edition (1989) Cold Spring Harbor Laboratory Press, Cold Spring Harbor, N.Y.).

More preferably hybridization occurs under the following conditions:

| | |
|---|---|
| Hybridization buffer: | 2 × SSC; 10 × Denhard's solution (Fikoll 400 + PEG + BSA; ratio 1:1:1); 0.1% SDS; 5 mM EDTA; 50 mM Na$_2$HPO$_4$; 250 µg/ml herring sperm DNA; 50 µg/ml tRNA; or 0.25 M sodiumphosphate buffer pH 7.2 1 mM EDTA 7% SDS |
| Hybridization temperature T = | 65 to 68° C. |
| Washing buffer: | 0.2 × SSC; 0.1% SDS |
| Washing temperature T = | 65 to 68° C. |

Nucleic acid molecules hybridizing to the molecules according to the invention may be isolated e.g. from genomic or from cDNA libraries produced in particular from rice cells or tissue.

The identification and isolation of such nucleic acid molecules may take place by using the molecules according to the invention or parts of these molecules or, as the case may be, the reverse complementary strands of these molecules, e.g. by hybridization according to standard methods (see e.g. Sambrook et al., 1989, *Molecular Cloning, A Laboratory Manual*, 2nd Edition, Cold Spring Harbor Laboratory Press, Cold Spring Harbor, N.Y.).

As a probe for hybridization e.g. nucleic acid molecules may be used which exactly or basically contain the nucleotide sequence indicated under Seq. ID No. 1 or parts thereof. The DNA fragments used as hybridization probe may also be synthetic DNA fragments which were produced by means of the conventional DNA synthesizing methods and the sequence of which is basically identical with that of a nucleic acid molecule of the invention. After identifying and isolating genes hybridizing to the nucleic acid sequences according to the invention, the sequence has to be determined and the properties of the proteins encoded by this sequence have to be analyzed.

Such hybridizing nucleic acid molecules also encompass fragments, derivatives and allelic variants of the above-mentioned nucleic acid molecules, which encode the above-mentioned protein. In this context fragments are described as parts of the nucleic acid molecules which are long enough in order to encode the above-described protein. The term derivative means that the sequences of these molecules differ from the sequences of the above-mentioned nucleic acid molecules at one or more positions and exhibit a high degree of homology to the sequences of these molecules. Homology means a sequence identity on the nucleotide level of at least 90%, in particular an identity of at least 93%, preferably of more than 95% and still more preferably a sequence identity of more than 98% and particularly preferred of more than 99%. Preferably, the degree of homology is determined by comparing the respective sequence with the nucleotide sequence of the coding region of SEQ ID NO:1. When the two sequences which are compared do not have the same length, the degree of homology preferably refers to the percentage of nucleotide residues in the shorter sequence which are identical to nucleotide residues in the longer sequence. The degree of homology can be determined conventionally using known computer programs such as the Bestfit program (Wisconsin Sequence Analysis Package, Version 8 for Unix, Genetics Computer Group, University Research Park, 575 Science Drive, Madison, Wis. 53711). Bestfit uses the local homology algorithm of Smith and Waterman, Advances in Applied Mathematics 2: 482-489 (1981), to find the best segment of homology between two sequences. When using Bestfit or any other sequence alignment program to determine whether a particular sequence is, for instance, 95% identical to a reference sequence according to the present invention, the parameters are set, preferably, such that the percentage of identity is calculated over the full length of the reference nucleotide sequence and that gaps in homology of up to 5% of the total number of nucleotides in the reference sequence are allowed. When using Bestfit the so-called "optional parameters" are, preferably, left at their default values. The deviations occurring when comparing a given sequence with the above-described nucleic acid molecules according to the invention might have been caused, e.g., by addition, deletion, substitution, insertion or recombination.

Furthermore, homology means preferably that the encoded protein displays a sequence identity of at least 90%, more preferably of at least 93%, even more preferably of at least 95%, in particular of at least 98% and particularly preferred of at least 99% to the amino acid sequence depicted under SEQ ID NO:2.

Preferably, sequences hybridizing to a nucleic acid molecule according to the invention comprise a region of homology of at least 90%, preferably of at least 93%, more preferably of at least 95%, still more preferably of at least 98% and particularly preferred of at least 99% identity to an above-described nucleic acid molecule, wherein this region of homology has a length of at least 500 nucleotides, more preferably of at least 600 nucleotides, even more preferably of at least 800 nucleotides and particularly preferred of at least 1000 nucleotides.

Moreover, homology means that functional and/or structural equivalence exists between the respective nucleic acid molecules or the proteins they encode. The nucleic acid molecules, which are homologous to the above-described nucleic acid molecules and represent derivatives of these molecules, are generally variations of these nucleic acid molecules, that constitute modifications which exert the same biological function. These variations may be naturally occurring variations or mutations, whereby these mutations may have occurred naturally or they may have been introduced deliberately. Moreover the variations may be synthetically produced sequences.

The allelic variants may be naturally occurring as well as synthetically produced variants or variants produced by recombinant DNA techniques.

In a further preferred embodiment the term "derivative" encompasses a nucleic acid molecule coding for a protein which exhibits a degree of homology to the amino acid sequence depicted under SEQ ID NO:2 of at least 60%, in particular a homology of at least 70%, preferably of more than 80% and still more preferably a homology of more than 90% and particularly preferred of more than 95% and which comprises at least one, more preferably at least three, even more preferably at least five, in particular at least ten and particularly preferred at least twenty of the peptide motifs selected from the group consisting of

| | | |
|---|---|---|
| (a) | PFIKS, | (SEQ ID NO:3) |
| (b) | QAIEF, | (SEQ ID NO:4) |
| (c) | NYAPE, | (SEQ ID NO:5) |
| (d) | ELQSE, | (SEQ ID NO:6) |
| (e) | KVAKNT, | (SEQ ID NO:7) |
| (f) | AADLV, | (SEQ ID NO:8) |

-continued

| (g) | QYQEI, | (SEQ ID NO:9) |
| (b) | ALLDY, | (SEQ ID NO:10) |
| (i) | DRPIH, | (SEQ ID NO:11) |
| (j) | QKDGL, | (SEQ ID NO:12) |
| (k) | IATCM, | (SEQ ID NO:13) |
| (l) | ARAEL, | (SEQ ID NO:14) |
| (m) | ALSTD, | (SEQ ID NO:15) |
| (n) | NRIDP, | (SEQ ID NO:16) |
| (o) | GYIVV, | (SEQ ID NO:17) |
| (p) | RNCKV, | (SEQ ID NO:18) |
| (q) | LGFPS, | (SEQ ID NO:19) |
| (r) | VILDY, | (SEQ ID NO:20) |
| (s) | FQKSI, | (SEQ ID NO:21) |
| (t) | EGAVK, | (SEQ ID NO:22) |
| (u) | VKEGK, and | (SEQ ID NO:23) |
| (v) | KLYVV, | (SEQ ID NO:24). |

The proteins encoded by the various variants of the nucleic acid molecules according to the invention exhibit certain common characteristics. Enzyme activity, molecular weight, immunologic reactivity, conformation etc. may belong to these characteristics as well as physical properties such as the mobility in gel electrophoresis, chromatographic characteristics, sedimentation coefficients, solubility, spectroscopic properties, stability, pH-optimum, temperature-optimum etc. Preferably, the R1-protein encoded by the nucleic acid molecules according to the invention has similar properties as the R1-protein from potato as described in Lorberth et al. (*Nature Biotechnology* 16 (1998), 473-477). In particular, the protein encoded by the nucleic acid molecules according to the invention is involved in the phosphorylation of starch. This property can be tested by expressing the nucleic acid molecules in *E. coli* and analyzing the phosphate content of the glycogen synthesized by the bacteria according to methods well known to the person skilled in the art or as described in WO 97/11188.

Preferably, the protein encoded by one of the above-described nucleic acid molecules is recognized by a polyclonal antibody obtainable by the following process:

A BamHI/BclI fragment from pSK-R1 (Lorberth et al., *Nature Biotechnology* 16 (1998), 473-477) is cloned in the BamHI restriction site of pET21d (Novagen) from which prior to the insertion of the RI fragment the HindIII restriction site is removed by religation of the filled-in HindIII site, in order to generate an R1 expression vector. For removal of the signal peptide coding sequence, a 900 bp fragment is amplified using the following two primers:

1) 5'-GAGA<u>CCATGG</u>TACTTACCACTGATACC-3' (NcoI restriction site is underlined) (SEQ ID NO: 25)
2) 5'-GTACTTGTACTGCAGGAC-3' (SEQ ID NO: 26)

The NcoI/HindIII cut PCR fragment is ligated into pET21dR1 for construction of PET21 dR1-tp. To produce recombinant protein, BL21(DE3) cells are transformed with this expression vector. R1protein expression is initiated by the addition of 1 mM IPTG (isopropyl-β-D-thiogalactoside) to the growth medium (terrific broth: 60 g tryptone, 120 g yeast extract, 20 ml 87% glycerin, 17 mM $KH_2PO_4$, 72 mM $K_2HPO_4$) when an $OD_{600}$ value of 0.5 is reached. Protein expression is continued for 3h at 37° C. before cells are pelleted by centrifugation. Cells are lysed by resuspension in sample buffer (Laemmli, *Nature* 227 (1970), 680-685). Protein extract is denatured by incubation for 5 min. at 95° C. and proteins are separated by SDS PAGE. After Coomassie staining the band corresponding to the ~160 kD R1 protein is excised from the gel, SDS is removed by incubation of the gel slices for 2 days in water. The gel slices are frozen, crushed and used for immunization.

PAA portions containing about 100 μg of R1 protein are used each time for injection. Rabbits are immunized 3 times. The first boost is performed one and the second two weeks after the first immunization. Final bleeding, yielding the antiserum is performed 2 weeks after the second boost. For Western analysis the antiserum is used in a 1:500 dilution.

Furthermore, the present invention relates to nucleic acid molecules the sequences of which, compared to the sequences of the above-mentioned molecules, are degenerated due to the genetic code and which encode a protein which is present in the plastids of plant cells.

The present invention also relates to the nucleotide sequences of intervening sequences (introns) which are present in genomic sequences corresponding to the nucleic acid molecules of the invention. Such intervening sequences can be isolated with the above-described nucleic acid molecules of the invention, e.g., by screening suitable genomic libraries.

The nucleic acid molecules of the invention can, for example, be isolated from natural sources, produced by methods of genetic engineering, e.g. by PCR, or produced by means of synthesis methods known to the skilled person.

The nucleic acid molecules of the invention may be DNA molecules, such as cDNA or genomic DNA, as well as RNA molecules. In particular, the nucleic acid molecules can also be genomic sequences from rice comprising the coding region of one of the above described nucleic acid molecules or parts thereof and/or intervening sequences (introns) of an R1 gene naturally occurring in rice.

Furthermore, the invention relates to vectors, especially plasmids, cosmids, viruses, bacteriophages and other vectors common in genetic engineering, which contain the above-mentioned nucleic acid molecules of the invention.

In a preferred embodiment the nucleic acid molecules contained in the vectors are linked to regulatory elements that ensure the transcription and synthesis of a translatable RNA in prokaryotic and eukaryotic cells.

In a further embodiment the invention relates to host cells, in particular prokaryotic or eukaryotic cells, which have been transformed and/or recombinantly manipulated by an above-mentioned nucleic acid molecule of the invention or by a vector of the invention, as well as cells which are derived from such cells and which contain a nucleic acid molecule of the invention or a vector of the invention. This is preferably a bacterial cell or a plant cell.

The protein encoded by the nucleic acid molecules of the invention influences the starch synthesis or modification of starch. Changes in the amount of the protein in plant cells lead to changes in the starch metabolism of the plant, especially to the synthesis of starch with modified physical and chemical properties.

A similar protein as that described in the present application was already described for potato (Lorberth et al., *Nature Biotechnology* 16 (1998), 473477; WO 97/11188) and for maize (WO 98/27212). However, for rice the existence of such a protein was not described. By providing the nucleic acid molecules of the invention it is possible to produce plants, in particular rice plants, by means of recombinant DNA techniques synthesizing a modified starch which differs from the starch synthesized in wildtype plants with respect to its structure and its physical and chemical properties which in turn influence the cooking properties of the rice grain. For this purpose, the nucleic acid molecules of the invention may be linked to regulatory elements, which ensure the transcription and translation in plant cells, and introduced into the plant cells.

Therefore, the present invention also relates to transgenic plant cells containing a nucleic acid molecule of the invention wherein the same is linked to regulatory elements which ensure the transcription in plant cells. The regulatory elements are preferably heterologous with respect to the nucleic acid molecule. In particular, the present invention also relates to plant cells in which the expression of a nucleic acid molecule according to the invention is increased in comparison to corresponding wild-type cells. Such an increase may, e.g., be detected by Northern Blot analysis. The term "increased" means preferably an increase of transcripts of the nucleic acid molecules of the invention of at least 10%, more preferably of at least 50% and even more preferably of at least 100%.

The invention also relates to plant cells in which the amount of the protein encoded by a nucleic acid molecule of the invention is increased in comparison to corresponding wild-type cells. Such an increase can, e.g., be detected by Western Blot analysis. Such an antibody may be a polyclonal antibody the production of which has been described above in connection with the properties of a protein according to the invention. The term "increased" means preferably an increase of the amount of the described protein of at least 10%, more preferably of at least 50% and even more preferably of at least 100%.

Such plant cells of the invention differ from naturally occurring plants among other things in that at least one copy of the nucleic acid molecule of the invention is integrated in their genome, possibly in addition to the naturally occurring copies. Furthermore, this/these additional copy/copies is/are preferably integrated at a location in the genome at which they do not occur naturally. This may be proved, for example, by means of a Southern Blot analysis. Furthermore, such transgenic plant cells can preferably be distinguished from corresponding naturally occurring plant cells by at least one of the following features: If the nucleic acid molecule according to the invention, which was introduced into the plant cells, is heterologous to the plant cells, the transgenic cells can be distinguished from non transformed cells due to the presence of transcripts from the introduced molecule according to the invention. Such transcripts can be detected, e.g., by Northern Blot analysis. Preferably the transgenic cells furthermore contain the protein encoded by the nucleic acid molecule according to the invention. The presence of the protein can be detected, e.g., by immunological methods such as Western Blot analysis.

If the nucleic acid molecule according to the invention which was introduced into the cells is homologous with respect to the cells, the transgenic cells can be distinguished from non-transformed cells, for example, due to the additional expression of the nucleic acid molecule according to the invention. In particular, the transgenic cells contain preferably more transcripts of the nucleic acid molecules according to the invention. This can be detected, e.g., by Northern Blot analysis. "More" preferably means at least 10% more, more preferably at least 20% more, and even more preferably at least 50% more. Accordingly, the transgenic cells contain preferably more protein according to the invention in comparison to non-transformed cells. This can be detected, e.g., by Western Blot analysis. Preferably, the cells contain at least 10% more protein according to the invention, more preferably at least 20% and even more preferably at least 50% more.

In a preferred embodiment the plant cells according to the present invention are cells of a starch storing tissue, preferably cells of tubers or endosperm tissue and even more preferably cells of the endosperm tissue of rice plants.

The protein encoded by a nucleic acid molecule according to the invention and expressed in the described cells is preferably located in the plastids of these cells. In order to ensure the location in the plastids it is conceivable to replace the first 40 to 120, more preferably the first 60 to 100 amino acid residues of the sequence depicted in SEQ ID NO:2 by another transit peptide responsible for translocation to the plastids. An example for such a peptide is the transit peptide of the plastidic Ferredoxin: $NADP^+$ oxidoreductase (FNR) of spinach which is enclosed in Jansen et al. (*Current Genetics* 13 (1988), 517-522). In particular, the sequence ranging from nucleotides −171 to 165 of the cDNA sequence disclosed therein can be used, which comprises the 5' nontranslated region as well as the sequence encoding the transit peptide. Another example is the transit peptide of the waxy protein of maize including the first 34 amino acid residues of the mature waxy protein (Klösgen et al., *Mol. Gen. Genet.* 217 (1989), 155-161). It is also possible to use this transit peptide without the first 34 amino acid-residues of the mature protein. Furthermore, the signal peptides of the ribulose biphosphate carboxylase small submit (Wolter et al., *Proc. Natl. Acad. Sci. USA* 85 (1988), 846-850; Nawrath et al., *Proc. Nat. Acad. Sci. USA* 91 (1994), 12760-12764), of the NADP malat dehydrogenase (Gallardo et al., *Planta* 197 (1995), 324-332) or of the glutathion reductase (Creissen et al., *Plant J.* 8 (1995), 167-175) can be used.

By means of methods known to the skilled person the transgenic plant cells can be regenerated to whole plants. The plants obtainable by regenerating the transgenic plant cells of the invention are also the subject-matter of the present invention.

A further subject-matter of the invention are plants which contain the above-described transgenic plant cells. The transgenic plants may in principle be plants of any desired species, i.e. they may be monocotyledonous as well as dicotyledonous plants. These are preferably useful plants, such as vegetables (e.g. tomato) and in particular starch-synthesizing or starch-storing plants such as cereals (rye, barley, oats, wheat, millet, sago etc.), maize, peas, wrinkled peas, cassava, potato, tomato, oil seed rape, soy bean, hemp, flax, sunflower, cowpea and arrowroot. The transgenic plants may also be pastures like white clover, ryegrass or alfalfa. Particularly preferred are rice, wheat, corn and potato plants.

In another preferred embodiment the plants according to the present invention display an increase in the expression of a nucleic acid molecule according to the invention and/or of the amount of the encoded protein and/or of its activity in cells of starch storing tissue when compared to corresponding wild-type plants. Preferably the starch storing tissue is tuber tissue or endosperm tissue.

In this context it should be pointed out that the term "wild-type plant" or "wild-type cells" in the scope of the present invention refers to plants or cells which were used as starting material for the production of the transgenic plants or cells according to the present invention, i.e. plants or cells which have the same genetic information as the transgenic plants or cells according to the invention except for the nucleic acid molecule(s) introduced in order to prepare such a plant or cell.

In a particularly preferred embodiment the transgenic plants of the present invention are rice plants.

The present invention also relates to a process for the production of a modified starch comprising the step of extracting from the above-described plants according to the invention and/or from starch storing parts of such plants the starch. Preferably, such a process furthermore comprises the steps of cultivating plants according to the invention and harvesting the cultivated plants and/or starch storing parts of these plants before the extraction of the starch.

Methods for extracting starch from plants or from starch storing parts of plants are well known to the person skilled in the art. Methods to extract starch, for example, from maize seeds are described, for example, in Eckhoff et al. (*Cereal Chem.* 73 (1996), 54-57). Extraction of maize starch on an industrial scale is normally achieved by "wet-milling". Furthermore, methods for the extraction of starch from various starch storing plants are described, for example, in *Starch: Chemistry and Technology* (eds.: Whistler, BeMiller and Paschall (1994) 2nd Edition, Academic Press Inc. London LTD; ISBN 0-12-746270-8; see e.g. Chapter XII, page 417-468: Corn and Sorghum Starches: Production; by Watson, S. A.; Chapter XIII, page 469-479: Tapioca, Arrowroot and Sago Starches: Production; by Corbishley and Miller; Chapter XIV, page 479-490: Potato Starch: Production and Uses; by Mitch; Chapter XV, page 491-506: Wheat starch: Production, Modification and Uses; by Knight and Olson; and Chapter XVI, page 507-528: Rice starch: Production and Uses; by Rohwer and Klem). Means usually used in methods for the extraction of starches from plant materials are separators, decanters, hydroclones and different kinds of machines for drying the starch, e.g., spray drier or jet drier.

The present invention also relates to the starch obtainable from the transgenic plant cells and plants of the invention or by the above described process. Due to the expression or the additional expression of a nucleic acid molecule of the invention, the transgenic plant cells and plants of the invention synthesize a starch which is modified when compared to starch from wildtype-plants, i.e. non-transformed plants.

In particular, such a starch has preferably a higher phosphate content than starch synthesized by corresponding non-transformed cells or plants. A higher phosphate content preferably means that the starch contains at least 10% more phosphate, more preferably at least 30%, even more preferably at least 50% and particularly preferred at least 100% more phosphate than starch from corresponding non-transformed cells or plants. The phosphate content of the starch can be determined as described, e.g., in Lorberth et al., supra, or Lim et al., *Cereal Chem.* 71 (1994), 488. Starches with a high content of phosphate can show an increased paste clarity and are of particular interest for the food industry and for the paper industry, e.g., for the preparation of the surface of paper. Normally, the paper industry uses chemically modified starch, for example, hydroxyethylated or phosphorylated starch, for the surface sizing or coating. The production of highly phosphorylated starch in plants would thus avoid the necessity to chemically modify starch in order to adapt it to the requirements of the paper industry.

Thus, the present invention also relates to starch the paste clarity of which is increased in comparison to that of starch of wild-type plants, preferably by at least 20%, more preferably by at least 50%, even more preferably by at least 100%, particularly preferred by at least 250% and most preferably by at least 500%. The paste clarity (light transparency) is determined by the following method: In order to determine the light transparency a starch/water suspension of 0.5% is prepared and heated for 15 min at 90° C. in order to induce pastification. Subsequently the absorption of the dispersion (at about 85° C.) is measured at 628 nm.

The present invention also relates to rice grains obtainable from transgenic rice plants according to the invention which preferably display an altered cooking quality and/or an enhanced nutritional value compared to grains of wildtype plants. Within the framework of the present invention the term "cooking quality" embraces properties such as cooking time, cooking rate, water absorption, volume expansion, (mechanical) hardness, stickiness, elongation of rice grain during cooking process. In a preferred embodiment the term "cooking quality" means that the rice grains according to the invention display a minimal cooking time that is reduced in comparison to that of grains of corresponding wild-type plants by at least 5%, preferably by at least 10%, more preferably by at least 20% and most preferably by at least 30% and/or it means that they display a water absorption rate that is increased in comparison to that of grains of corresponding wild-type plants by at least 1%, preferably by at least 2%, more preferably by at least 5% and most preferably by at least 10%. The minimal cooking time can be determined according to the method of Ranghino (*Riso* 15 (1969), 117-127). The determination of the water absorption rate can, e.g., be done as described by Juliano (*IRRI Res. Paper Ser.* 77, Int. Rice Res. Inst. Los Banos, Laguna, Philippines, 28 pp) or by Halick and Kelly (*Cereal Chemistry* 36 (1959), 91-98). The term "nutritional value" is associated with the quantity of available micronutrients, like iron and zinc in the rice grain. In a preferred embodiment of the invention the amount of zinc and/or iron and/or micronutrients in the rice grain is increased. In this context the term "increased" means an increase of at least 1%, preferably of at least 5%, even more preferably of at least 10% and most preferably of at least 20% of the amount of zinc, iron or micronutrients when compared to corresponding wild-type plants.

Methods for the determination of the amount of micronutrients, zinc and iron are well known to the person skilled in the art.

A further subject-matter of the present invention is a method for the production of an R1-protein from rice in which host cells of the invention are cultivated under conditions that allow for the expression of the protein and in which the protein is then isolated from the cultivated cells and/or the culture medium.

Furthermore, the invention relates to proteins encoded by the nucleic acid molecules of the invention as well as to proteins obtainable by the above-described method. These are preferably proteins from rice encoded by nuclear genes and which are localized in the plastids.

A further subject-matter of the invention are antibodies which specifically recognize a protein of the invention. These may be monoclonal as well as polyclonal antibodies. Methods for the production of such antibodies are known to the skilled person.

Furthermore, it is possible to influence the properties of the starch synthesized in plant cells by reducing the amount of proteins encoded by the nucleic acid molecules according to the invention in the cells. This reduction may be effected, for example, by means of antisense expression of the nucleic acid molecules of the invention, expression of suitable ribozymes, a cosuppression effect or by the so-called "in vivo mutagenesis". In an embodiment of this invention, the protein amount is reduced relative to the amount of protein observed in a corresponding wild-type plant cell.

Therefore, DNA molecules encoding an antisense RNA which is complementary to transcripts of a DNA molecule of the invention or to sequences of (an) intron(s) of the corresponding genomic sequences are also the subject-matter of the present invention, as well as these antisense molecules. In order to cause an antisense-effect during the transcription in plant cells such DNA molecules have a length of at least 15 bp, preferably a length of more than 100 bp and most preferably a length of more than 500 bp, however, usually less than 5000 bp, preferably shorter than 2500 bp.

The invention further relates to DNA molecules which, during expression in plant cells, lead to the synthesis of an RNA which in the plant cells due to a cosuppression-effect reduces the expression of the nucleic acid molecules of the invention encoding the described protein. Such DNA molecules may comprise the coding region of a nucleic acid molecule of the invention or parts thereof and/or sequences of (an) intron(s) of a corresponding genomic sequence. The invention also relates to RNA molecules encoded thereby. The general principle of cosuppression and the corresponding method is well known to the person skilled in the art and is described, for example, in Jorgensen (*Trends Biotechnol.* 8 (1990), 340-344), Niebel et al. (*Curr. Top. Microbiol. Immunol.* 197 (1995), 91-103), Flavell et al. (*Curr. Top. Microbiol. Immunol.* 197 (1995), 43-56), Palaqui and Vaucheret (*Plant. Mol. Biol.* 29 (1995), 149-159), Vaucheret et al. (*Mol. Gen. Genet.* 248 (1995), 311-317) and de Borne et al. (*Mol. Gen. Genet.* 243 (1994), 613-621), Smyth (*Curr. Biol.* 7 (1997), R793-R795) and Taylor, *Plant Cell* 9 (1997), 1245-1249).

For inhibiting the expression of a nucleic acid molecule according to the invention in rice plant cells with the help of the above-described antisense approach or with the cosuppression approach, DNA molecules are preferably used which display a degree of homology of at least 90%, more preferably of at least 93%, even more preferably of at least 95% and most preferably of at least 98% with the nucleotide sequence depicted in SEQ ID NO: 1.

In a further embodiment the present invention relates to DNA molecules encoding an RNA molecule with ribozyme activity which specifically cleaves transcripts of a DNA molecule of the invention as well as these encoded RNA molecules.

Ribozymes are catalytically active RNA molecules capable of cleaving RNA molecules and specific target sequences. By means of recombinant DNA techniques it is possible to alter the specificity of ribozymes. There are various classes of ribozymes. For practical applications aiming at the specific cleavage of the transcript of a certain gene, use is preferably made of representatives of two different groups of ribozymes. The first group is made up of ribozymes which belong to the group I intron ribozyme type. The second group consists of ribozymes which as a characteristic structural feature exhibit the so-called "hammerhead" motif. The specific recognition of the target RNA molecule may be modified by altering the sequences flanking this motif. By base pairing with sequences in the target molecule these sequences determine the position at which the catalytic reaction and therefore the cleavage of the target molecule takes place. Since the sequence requirements for an efficient cleavage are low, it is in principle possible to develop specific ribozymes for practically each desired RNA molecule.

In order to produce DNA molecules encoding a ribozyme which specifically cleaves transcripts of a DNA molecule of the invention, for example a DNA sequence encoding a catalytic domain of a ribozyme is bilaterally linked with DNA sequences which are homologous to sequences of the target enzyme. Sequences encoding the catalytic domain may for example be the catalytic domains of the satellite DNA of the SCMo virus (Davies et al., *Virology* 177 (1990), 216-224) or that of the satellite DNA of the TobR virus (Steinecke et al., *EMBO J.* 11 (1992), 1525-1530; Haseloff and Gerlach, *Nature* 334 (1988), 585-591). The DNA sequences flanking the catalytic domain are preferably derived from the above-described DNA molecules of the invention. The general principle of the expression of ribozymes and the method is described, for example, in EP-BI 0 321 201. The expression of ribozymes in plant cells is described, e.g., in Feyter et al. (*Mol. Gen. Genet.* 250 (1996), 329-338).

A reduction of the activity of the protein according to the invention in plant cells can also be achieved by the so-called "in vivo mutagenesis" (also known as "Chimeraplasty"). In this method a hybrid RNA/DNA oligonucleotide (chimeroplast) is introduced into cells (Kipp et al., Poster Session at the 5th International Congress of Plant Molecular Biology, Sep. 21 to 27, 1997, Singapore; Dixon and Arntzen, meeting report on "Metabolic Engineering in Transgenic Plants", Keystone Symposia, Copper Mountain, Colo., USA, *TIBTECH* 15 (1997), 441-447; international patent application WO 95/15972; Kren et al., *Hepatology* 25 (1997), 1462-1468; Cole-Strauss et al., *Science* 273 (1996), 1386-1389; Zhu et al., *Proc. Natl. Acad. Sci. USA* 96 (1999), 8768-8773). A part of the DNA component of the RNA/DNA oligonucleotide is homologous to a nucleotide sequence occurring endogenously in the plant cell and encoding a protein according to the invention but displays a mutation or comprises a heterologous part which lies within the homologous region. Due to base pairing of the regions of the RNA/DNA oligonucleotide which are homologous to the endogenous sequence with these sequences, followed by homologous recombination, the mutation contained in the DNA component of the oligonucleotide can be introduced into the plant cell genome. This leads to a reduction of the activity of a protein according to the invention.

In a further embodiment the present invention relates to vectors containing the above-described DNA molecules, in particular those in which the described DNA molecules are linked with regulatory elements ensuring the transcription in plant cells.

Furthermore, the present invention relates to host cells containing the described DNA molecules or vectors. The host cell may be a prokaryotic cell, such as a bacterial cell, or a eukaryotic cell. The eukaryotic host cells are preferably plant cells.

Furthermore, the invention relates to transgenic plant cells in which the presence or expression of a foreign nucleic acid molecule leads to the inhibition of the expression of endogenous genes encoding a protein according to the invention.

In a preferred embodiment the foreign nucleic acid molecule is selected from the group consisting of:
(a) DNA molecules encoding an antisense-RNA which can lead to a reduction of the expression of endogenous genes encoding a protein according to the invention;
(b) DNA molecules which can lead to a reduction of the expression of endogenous genes encoding a protein according to the invention via a cosuppression-effect;
(c) DNA molecules encoding a ribozyme which can specifically cleave transcripts of endogenous genes encoding a protein according to the invention; and
(d) via in vivo mutagenesis introduced nucleic acid molecules, which lead to a mutation or to an insertion of a heterologous sequence in an endogenous gene encoding a protein according to the invention thereby leading to a reduction of the expression of the protein according to the invention or to the synthesis of an inactive protein.

These transgenic plant cells may be regenerated to whole plants according to well-known techniques. Thus, the invention also relates to plants which may be obtained through regeneration from the described transgenic plant cells, as well as to plants containing the described transgenic plant cells. The transgenic plants themselves may be plants of any desired plant species, preferably useful plants, such as vegetables (e.g. tomato) and particularly starch-storing ones, as indicated above, and most preferably rice, corn, wheat and potato plant cells.

Furthermore, the invention relates to the antisense RNA molecules encoded by the described DNA molecules, as well as to RNA molecules with ribozyme activity and RNA molecules which lead to a cosuppression effect which are obtainable, for example, by means of transcription.

A further subject-matter of the invention is a method for the production of transgenic plant cells, which in comparison to non-transformed cells synthesize a modified starch. In this method the amount of proteins encoded by the DNA molecules of the invention, which are present in the cells in endogenic form, is reduced in the plant cells.

In a preferred embodiment this reduction is effected by means of an antisense effect. For this purpose the DNA molecules of the invention or parts thereof are linked in antisense orientation with a promoter ensuring the transcription in plant cells and possibly with a termination signal ensuring the termination of the transcription as well as the polyadenylation of the transcript. Possible is also the use of sequences of (an) intron(s) of corresponding genomic sequences. In order to ensure an efficient antisense effect in the plant cells the synthesized antisense RNA should exhibit a minimum length of 15 nucleotides, preferably of at least 100 nucleotides and most preferably of at least 500 nucleotides. Furthermore, the DNA sequence encoding the antisense RNA should be homologous with respect to the plant species to be transformed.

In a further embodiment the reduction of the amount of proteins encoded by the DNA molecules of the invention is effected by a ribozyme effect. The basic effect of ribozymes as well as the construction of DNA molecules encoding such RNA molecules have already been described above. In order to express an RNA with ribozyme activity in transgenic cells the above described DNA molecules encoding a ribozyme are linked with DNA elements which ensure the transcription in plant cells, particularly with a promoter and a termination signal. The ribozymes synthesized in the plant cells lead to the cleavage of transcripts of DNA molecules of the invention which are present in the plant cells in endogenic form.

A further possibility in order to reduce the amount of proteins encoded by the nucleic acid molecules of the invention is cosuppression. Therefore, the plant cells obtainable by the method of the invention are a further subject matter. These plant cells are characterized in that their amount of proteins encoded by the DNA molecules of the invention is reduced and that in comparison to wildtype cells they synthesize a modified starch.

Preferably, the transgenic cells show a reduction in the amount of transcripts encoding a protein according to the present invention of at least 30%, more preferably of at least 50%, even more preferably of at least 70% and most preferably of at least 90% in comparison to corresponding non-transformed cells. The amount of transcripts can be determined, for example, by Northern Blot analysis. Furthermore, the cells preferably show a corresponding reduction of the amount of the protein according to the invention. This can be determined, for example, by immunological methods such as Western Blot analysis. An example for an antibody which can be used in such a Western Blot analysis is a polyclonal antibody the production of which has been described above in connection with the properties of the protein according to the invention.

Furthermore, the plant cells to which such a method is applied is a rice plant cell.

Furthermore, the invention relates to plants obtainable by regeneration of the described plant cells as well as to plants containing the described cells of the invention.

The present invention also relates to a process for the production of a modified starch comprising the step of extracting from the above-described plants according to the invention and/or from starch storing parts of such plants the starch. Preferably, such a process furthermore comprises the steps of cultivating plants according to the invention; and harvesting the cultivated plants and/or starch storing parts of these plants before the extraction of the starch.

The present invention also relates to the starch obtainable from the described transgenic plant cells and plants or obtainable by the above described process. Due to the expression of the described DNA molecules encoding antisense RNA, a ribozyme or a cosuppression RNA in the transgenic plant cells the amount of proteins encoded by the DNA molecules of the invention which are present in the cells in endogenic form, is reduced. Preferably, this reduction leads to a drastic change of the physical and chemical properties of the starch synthesized in the plant cells. When compared to starch from non-transformed cells or plants the modified starch preferably exhibits altered pastification properties, i.e. an altered viscosity of the watery solutions of the starch and/or an altered, in particular a reduced phosphate content. In a preferred embodiment the phosphate content is reduced by at least 5%, more preferably by at least 20% and even more preferably by at least 50% in comparison to starch obtainable from corresponding non-transformed plant cells or plants. The phosphate content can be determined as described herein above.

The present invention furthermore relates to rice grains obtainable from the above described transgenic rice plants according to the invention which display an altered cooking quality compared to grains of wildtype plants. Within the framework of the present invention the term "cooking quality" embraces properties such as cooking time, cooking rate, water absorption, volume expansion, (mechanical) hardness, stickiness, elongation of rice grain during cooking process.

Preferably, the term "cooking qualities" means that the rice grains according to the invention display a reduction of water absorption of at least 1%, preferably of at least 2%, more preferably of at least 5% and even more preferably at least 10% when compared to grains of corresponding wild-type plants. Methods for determining the degree of water absorption of grains are well known to the person skilled in the art.

The expression of the nucleic acid molecules of the invention may in principle take place in any kind of plant species. Monocotyledonous and dicotyledonous plants are preferred, in particular useful plants, such as vegetables (e.g. tomato), and preferably starch-storing plants such as cereals (rye, barley, oats, wheat, millet, sago etc.), rice, maize, peas, wrinkled peas, cassaya, potato, tomato, oilseed rape, soy bean, hemp, flax, sunflower, cow-pea, arrowroot, and pastures, such as clover, ryegrass and alfalfa.

Particularly preferred are rice, corn, wheat and potato plants. Within the framework of the present invention the term "regulatory DNA elements ensuring the transcription in plant cells" are DNA regions which allow for the initiation or the termination of transcription in plant cells. DNA regions ensuring the initiation of transcription are in particular promoters.

For the expression of the various above-described DNA molecules of the invention in plants any promoter functioning in plant cells may be used. The promoter may be homologous or heterologous with respect to the used plant species. Use may, for example, be made of the 35S promoter of the cauliflower mosaic virus (Odell et al., *Nature* 313 (1985), 810-812; Mitsuhara et la., *Plant and Cell Physiology* 37 (1996), 49-59) which ensures a constitutive expression in all plant tissues and also of the promoter construct described in WO/9401571. However, use may also be made of promoters which lead to an expression of subsequent sequences only at a point of time determined by exogenous factors (such as in WO/9307279) or in a particular tissue of the plant (see e.g. Stockhaus et al., *EMBO J.* 8 (1989), 2245-2251). Promoters which are active in the starch-storing parts of the plant to be transformed are preferably used. In the case of maize these parts are the maize seeds, in the case of potatoes the tubers. In order to transform potatoes the tuber-specific B33-promoter (Rocha-Sosa et al., *EMBO J.* 8 (1989), 23-29) may be used particularly, but not exclusively. Apart from promoters, DNA regions initiating transcription may also contain DNA sequences ensuring a further increase of transcription, such as the so-called enhancer-elements. For expression in plant cells, and in particular in rice cells, the following promoters can be used: the 35S promoter (Odell et al. supra; Mitsuhara et al., supra), the ubiquitin promoter (U.S. Pat. No. 5,614,399; Christensen et al., *Plant Mol. Biol.* 18 (1992), 675-689; Takimoto et al., *Plant Mol. Biol.* 26 (1994), 1007-1012; Comejo et al., *Plant Mol. Biol.* 23 (1993), 567-581; Toki et al., *Plant Phys.* 100 (1992), 1503-1507), for an endosperm specific expression the glutelin promoter (Leisy et al., *Plant Mol. Biol.* 14 (1990), 41-50; Zbeng et al., *Plant J.* 4 (1993), 357-366; Kononowicz et al., Joint annual meeting of The American Society of Plant Physiologists and The Canadian Society of Plant Physiologists, Minneapolis, Minn., USA, Jul. 1 to Aug. 4, 1993, Plant Physiol. 102 (suppl.) (1993) 166; Zhao et al., Annual Meeting of the American Society of Plant Physiologists, Pittsburgh, Pa., USA, Aug. 1 to 5, 1992. *Plant Physiol.* 99 (1 Suppl.) (1992), 85; Yoshihara et al., *FEBS Lett.* 383 (1996), 213-218), the HMG promoter, the promoters of the zein gene from maize (Pedersen et al., *Cell* 29 (1982), 1015-1026; Quatroccio et al., *Plant Mol. Biol.* 15(1990), 81-93), the shrunken-1 promoter (Werr et al., *EMBO J.* 4 (1985), 1373-1380), furthermore the actin promoter (McElroy et al., *Plant Cell* 2 (1990), 163-171), the cab-6 promoter (*Plant and Cell Physiology* 35 (1994), 773-778), the RTBV promoter (Yin et al., *Plant J.* 12 (1997), 1179-1188), the CVMV promoter (Verdaguer et al., *Plant Mol. Biol.* 31 (1996), 1129-1139), the rab 16B promoter (*Plant Physiol.* 112 (1996), 483-491), the promoter of the psbD-C operon (To et al., *Plant and Cell Physiology* 37 (1996), 660-666), the Tpi promoter (Snowden et al., *Plant Mol. Biol.* 31 (1996), 689-692), the Osgrpl promoter (Xu et al., *Plant Mol. Biol.* 28 (1995), 455-471), the Ltp2 promoter (Kalla et al., *Plant J.* 6 (1994), 849-860), the ADH1 promoter (Kyozuka et al., *Mol. Gen. Genet.* 228 (1991), 40-48) and the LHCP promoter (*EMBO J.* 10 (1991), 1803-1808). For an expression in photosynthetically active cells the Ca/b promoter (see, e.g., U.S. Pat. Nos. 5,656,496; 5,639, 952; Bansal et al., *Proc. Natl. Acad. Sci. USA* 89 (1992), 3654-3658) and the Rubisco SSU promoter (see, e.g., U.S. Pat. Nos. 5,034,322 and 4,962,028) can be used. For seed specific expression the USP promoter of Vicia faber (Fiedler et al., *Plant Mol. Biol.* 22 (1993), 669-679; Bäumlein et al., *Mol. Gen. Genet.* 225 (1991), 459-467) can be used.

Furthermore, the term "regulatory DNA elements" may also comprise termination signals which serve to correctly end the transcription and to add a poly-A-tail to the transcript which is believed to stabilize the transcripts. Such elements are described in the literature and can be exchanged as desired. Examples for such termination sequences are the 3'-nontranslatable regions comprising the polyadenylation signal of the nopaline synthase gene (NOS gene) or the octopine synthase gene (Gielen et al., *EMBO J.* 8 (1989), 23-29) from agrobacteria, or the 3'-nontranslatable regions of the genes of the storage proteins from soy bean as well as the genes of the small subunit of ribulose-1,5-biphosphate-carboxylase (ssRUBISCO).

The introduction of the DNA molecules of the invention into plant cells is preferably carried out using plasmids. Plasmids ensuring a stable integration of the DNA into the plant genome are preferred.

In order to prepare the introduction of foreign genes in higher plants a large number of cloning vectors are at disposal, containing a replication signal for *E. coli* and a marker gene for the selection of transformed bacterial cells. Examples for such vectors are pBR322, pUC series, M13 mp series, pACYC184 etc. The desired sequence may be integrated into the vector at a suitable restriction site. The obtained plasmid is used for the transformation of *E. coli* cells. Transformed *E. coli* cells are cultivated in a suitable medium and subsequently harvested and lysed. The plasmid is recovered by means of standard methods. As an analyzing method for the characterization of the obtained plasmid DNA use is generally made of restriction analysis and sequence analysis. After each manipulation the plasmid DNA may be cleaved and the obtained DNA fragments may be linked to other DNA sequences.

In order to introduce DNA into plant host cells a wide range of techniques are at disposal. These techniques comprise the transformation of plant cells with T-DNA by using *Agrobacterium tumefaciens* or *Agrobacterium rhizogenes* as transformation medium, the fusion of protoplasts, the injection and the electroporation of DNA, the introduction of DNA by means of the biolistic method as well as further possibilities.

In the case of injection and electroporation of DNA into plant cells, there are no special demands made to the plasmids used. Simple plasmids such as pUC derivatives may be used. However, in case that whole plants are to be regenerated from cells transformed in such a way, a selectable marker gene should be present.

Depending on the method of introducing desired genes into the plant cell, further DNA sequences may be necessary. If the Ti- or Ri-plasmid is used e.g. for the transformation of the plant cell, at least the right border, more frequently, however, the right and left border of the Ti- and Ri-plasmid T-DNA has to be connected to the foreign gene to be introduced as a flanking region.

If Agrobacteria are used for transformation, the DNA which is to be introduced must be cloned into special plasmids, namely either into an intermediate vector or into a binary vector. Due to sequences homologous to the sequences within the T-DNA, the intermediate vectors may be integrated into the Ti- or Ri-plasmid of the Agrobacterium due to homologous recombination. This also contains the vir-region necessary for the transfer of the T-DNA. Intermediate vectors cannot replicate in Agrobacteria. By means of a helper plasmid the intermediate vector may be transferred to Agrobacterium tumefaciens (conjugation). Binary vectors may replicate in *E. coli* as well as in Agrobacteria. They contain a selectable marker gene as well as a linker or polylinker which is framed by the right and the left T-DNA border region. They may be transformed directly into the Agrobacteria (Holsters et al. *Mol. Gen. Genet.* 163 (1978), 181-187). The plasmids used for the transformation of the Agrobacteria further comprise a selectable marker gene, such as the NPT II gene which allows for selecting transformed bacteria. The plasmid may comprise further selection marker genes such as those conferring resistance against spectinomycin (Svab et al., *Proc. Natl. Acad. Sci. U.S.A.* 87 (1990), 8526-8530; Svab et al., *Plant. Mol. Biol.* 14 (1990), 197-206), against streptomycin (Jones et al., *Mol. Gen. Genet.* 91 (1987), 86-91; Svab et al., *Proc. Natl. Acad. Sci. U.S.A.* 87 (1990), 8526-8530; Svab et al., *Plant. Mol. Biol.* 14 (1990), 197-206), against phosphinotricin (De Block et al., *EMBO J.* 6 (1987), 2513-2518), against glyphosate (Thompson et al., *EMBO J.* 6 (1987), 2519-2523; Thompson et al., *Weed Sci.* 35 (1987), 19-23 (suppl.)) or against hygromycin (Waldron et al., *Plant Mol. Biol.* 5 (1985), 103-108). The Agrobacterium acting as host cell should contain a plasmid carrying a vir-region. The vir-region is necessary for the transfer of the T-DNA into the plant cell. Additional T-DNA may be present. The Agrobacterium transformed in such a way is used for the transformation of plant cells.

The use of T-DNA for the transformation of plant cells was investigated intensely and described sufficiently in EP 120 516; Hoekema, In: The Binary Plant Vector System Offset-drukkerij Kanters B.V., Alblasserdam (1985), Chapter V; Fraley et al., *Crit. Rev. Plant. Sci.*, 4, 1-46 and An et al. *EMBO J.* 4 (1985), 277-287. Some binary vectors may already be obtained commercially, such as pBIN19 (Clontech Laboratories, Inc., USA).

For transferring the DNA into the plant cells, plant explants may suitably be co-cultivated with *Agrobacterium tumefaciens* or *Agrobacterium rhizogenes*. From the infected plant material (e.g. pieces of leaves, stem segments, roots, but also protoplasts or suspension-cultivated plant cells) whole plants may then be regenerated in a suitable medium which may contain antibiotics or biocides for the selection of transformed cells. The plants obtained in such a way may then be examined as to whether the introduced DNA is present or not. Other possibilities in order to introduce foreign DNA by using the biolistic method or by transforming protoplasts are known to the skilled person (cf. e.g. Willmitzer, L., 1993 Transgenic plants. In: Biotechnology, A Multi-Volume Comprehensive Treatise (H.J. Rehm, G. Reed, A. Pühler, P. Stadler, editors), Vol. 2, 627-659, VCH Weinheim-New York-Basel-Cambridge).

Whereas the transformation of dicotyledonous plants by Ti-plasmid-vector systems by means of *Agrobacterium tumefaciens* is a well-established method, more recent studies indicate that the transformation with vectors based on Agrobacterium can also be used in the case of monocotyledonous plants (Chan et al., *Plant Mol. Biol.* 22 (1993), 491-506; Hici et al., *Plant J.* 6 (1994), 271-282).

Alternative systems for the transformation of monocotyledonous plants are the transformation by means of the biolistic approach, protoplast transformation, electroporation of partially permeabilized cells, the introduction of DNA by means of glass fibers.

There are various references in the relevant literature dealing specifically with the transformation of maize (cf e.g. WO95/06128, EP 0 513 849; EP 0 465 875). In EP 292 435 a method is described by means of which fertile plants may be obtained starting from mucousless, friable granulous maize callus. In this context it was furthermore observed by Shillito et al. (*Bio/Technology* 7 (1989), 581) that for regenerating fertile plants it is necessary to start from callus-suspension cultures from which a culture of dividing protoplasts can be produced which is capable to regenerate to plants. After an in vitro cultivation period of 7 to 8 months Shillito et al. obtain plants with viable descendants which, however, exhibited abnormalities in morphology and reproductivity. Prioli and Söndahl (*Bio/Technology* 7 (1989), 589) have described how to regenerate and to obtain fertile plants from maize protoplasts of the Cateto maize inbreed Cat 100-1. The authors assume that the regeneration of protoplast to fertile plants depends on a number of various factors such as the genotype, the physiological state of the donor-cell and the cultivation conditions. With regard to rice various transformation methods can be applied, e.g. the transformation by agrobacterium-medicated gene transfer (Hiei et al., *Plant J.* 6 (1994), 271-282; Hiei et al., *Plant Mol. Biol.* 35 (1997), 205-218; Park et al., *J. Plant Biol.* 38 (1995), 365-371), protoplast transformation (Datta in "Gene transfer to plants", I. Potrykus, G. Spangenberg (Eds), *Springer-Verlag Berlin Heidelberg*, 1995, pages 66-75; Datta et al., *Plant Mol. Biol.* 20 (1992), 619-629; Sadasivam et al., *Plant Cell Rep.* (1994), 394-396) the biolistic approach (Li et al., *Plant Cell Rep.* 12 (1993), 250-255; Cao et al., *Plant Cell Rep.* 11 (1992), 586-591; Christou, *Plant Mol. Biol.* (1997), 197-203) and electroporation (Xu et al., in "Gene transfer to plants", I. Potrykus, G. Spangenberg (Eds), *Springer-Verlag Berlin Heidelberg* (1995), 201-208).

Once the introduced DNA has been integrated in the genome of the plant cell, it usually continues to be stable there and also remains within the descendants of the originally transformed cell. It usually contains a selectable marker which confers resistance against biocides or against an antibiotic such as kanamycin, G 418, bleomycin, hygromycin or phosphinotricine etc. to the transformed plant cells. The individually selected marker should therefore allow for a selection of transformed cells against cells lacking the introduced DNA. The transformed cells grow in the usual way within the plant (see also McCormick et al., *Plant Cell Reports* 5 (1986), 81-84). The resulting plants can be cultivated in the usual way and cross-bred with plants having the same transformed genetic heritage or another genetic heritage. The resulting hybrid individuals have the corresponding phenotypic properties. Two or more generations should be grown in order to ensure whether the phenotypic feature is kept stably and whether it is transferred. Furthermore, seeds should be harvested in order to ensure that the corresponding phenotype or other properties will remain.

Due to its properties the starch obtainable from the plant cells or from the plants of the invention or obtainable by the processes of the invention is not only suitable for the specific purposes already mentioned herein, but also for various industrial uses.

Basically, starch can be subdivided into two major fields. One field comprises the hydrolysis products of starch and the so-called native starches. The hydrolysis products essentially comprise glucose and glucans components obtained by enzymatic or chemical processes. They can be used for further processes, such as fermentation and chemical modifications. In this context, it might be of importance that the hydrolysis process can be carried out simply and inexpensively. Currently, it is carried out substantially enzymatically using amyloglucosidase. It is thinkable that costs might be reduced by using lower amounts of enzymes for hydrolysis due to changes in the starch structure, e.g. increasing the surface of the grain, improved digestibility due to less branching or a steric structure, which limits the accessibility for the used enzymes.

The use of the so-called native starch which is used because of its polymer structure can be subdivided into two further areas:

(a) Use in Foodstuffs

Starch is a classic additive for various foodstuffs, in which it essentially serves the purpose of binding aqueous additives and/or causes an increased viscosity or an increased gel formation. Important characteristic properties are flowing and sorption behavior, swelling and pastification temperature, viscosity and thickening performance, solubility of the starch, transparency and paste structure, heat, shear and acid resistance, tendency to retrogradation, capability of film formation, resistance to freezing/thawing, digestibility as well as the capability of complex formation with e.g. inorganic or organic ions. The starch according to the present invention in particular that obtainable from rice can, e.g., be used for the preparation of noodles referred to as Chinese noodles or Asia noodles. Moreover, the starch according to the invention may be used as a fat replacer.

(b) Use in Non-Foodstuffs

The other major field of application is the use of starch as an adjuvant in various production processes or as an additive in technical products. The major fields of application for the use of starch as an adjuvant are, first of all, the paper and cardboard industry. In this field, the starch is mainly used for retention (holding back solids), for sizing filler and fine particles, as solidifying substance and for dehydration. In addition, the advantageous properties of starch with regard to stiffness, hardness, sound, grip, gloss, smoothness, tear strength as well as the surfaces are utilized.

Within the paper production process, a differentiation can be made between four fields of application, namely surface, coating, mass and spraying.

The requirements on starch with regard to surface treatment are essentially a high degree of brightness, corresponding viscosity, high viscosity stability, good film formation as well as low formation of dust. When used in coating the solid content, a corresponding viscosity, a high capability to bind as well as a high pigment affinity play an important role. As an additive to the mass rapid, uniform, loss-free dispersion, high mechanical stability and complete retention in the paper pulp are of importance. When using the starch in spraying, corresponding content of solids, high viscosity as well as high capability to bind are also significant.

A major field of application is, for instance, in the adhesive industry, where the fields of application are subdivided into four areas: the use as pure starch glue, the use in starch glues prepared with special chemicals, the use of starch as an additive to synthetic resins and polymer dispersions as well as the use of starches as extenders for synthetic adhesives. 90% of all starch-based adhesives are used in the production of corrugated board, paper sacks and bags, composite materials for paper and aluminum, boxes and wetting glue for envelopes, stamps, etc.

Another possible use as adjuvant and additive is in the production of textiles and textile care products. Within the textile industry, a differentiation can be made between the following four fields of application: the use of starch as a sizing agent, i.e. as an adjuvant for smoothing and strengthening the burring behavior for the protection against tensile forces active in weaving as well as for the increase of wear resistance during weaving, as an agent for textile improvement mainly after quality-deteriorating pretreatments, such as bleaching, dying, etc., as thickener in the production of dye pastes for the prevention of dye diffusion and as an additive for warping agents for sewing yarns.

Furthermore, starch may be used as an additive in building materials. One example is the production of gypsum plaster boards, in which the starch mixed in the thin plaster pastifies with the water, diffuses at the surface of the gypsum board and thus binds the cardboard to the board. Other fields of application are admixing it to plaster and mineral fibers. In ready-mixed concrete, starch may be used for the deceleration of the sizing process.

Furthermore, the starch is advantageous for the production of means for ground stabilization used for the temporary protection of ground particles against water in artificial earth shifting. According to state-of-the-art knowledge, combination products consisting of starch and polymer emulsions can be considered to have the same erosion- and encrustation-reducing effect as the products used so far; however, they are considerably less expensive.

Another field of application is the use of starch in plant protectives for the modification of the specific properties of these preparations. For instance, starches are used for improving the wetting of plant protectives and fertilizers, for the dosed release of the active ingredients, for the conversion of liquid, volatile and/or odorous active ingredients into microcristalline, stable, deformable substances, for mixing incompatible compositions and for the prolongation of the duration of the effect due to a reduced disintegration.

Starch may also be used in the fields of drugs, medicine and in the cosmetics industry. In the pharmaceutical industry, the starch may be used as a binder for tablets or for the dilution of the binder in capsules. Furthermore, starch is suitable as disintegrant for tablets since, upon swallowing, it absorbs fluid and after a short time it swells so much that the active ingredient is released. For qualitative reasons, medicinal flowance and dusting powders are further fields of application. In the field of cosmetics, the starch may for example be used as a carrier of powder additives, such as scents and salicylic acid. A relatively extensive field of application for the starch is toothpaste.

The use of starch as an additive in coal and briquettes is also thinkable. By adding starch, coal can be quantitatively agglomerated and/or briquetted in high quality, thus preventing premature disintegration of the briquettes. Barbecue coal contains between 4 and 6% added starch, calorated coal between 0.1 and 0.5%. Furthermore, the starch is suitable as a binding agent since adding it to coal and briquette can considerably reduce the emission of toxic substances.

Furthermore, the starch may be used as a flocculant in the processing of ore and coal slurry.

Another field of application is the use as an additive to process materials in casting. For various casting processes cores produced from sands mixed with binding agents are needed. Nowadays, the most commonly used binding agent is bentonite mixed with modified starches, mostly swelling starches.

The purpose of adding starch is increased flow resistance as well as improved binding strength. Moreover, swelling starches may fulfill more prerequisites for the production process, such as dispersability in cold water, rehydratisability, good mixability in sand and high capability of binding water.

In the rubber industry starch may be used for improving the technical and optical quality. Reasons for this are improved surface gloss, grip and appearance. For this purpose, the starch is dispersed on the sticky rubberized surfaces of rubber substances before the cold vulcanization. It may also be used for improving the printability of rubber.

Another field of application for the modified starch is the production of leather substitutes.

In the plastics market the following fields of application are emerging: the integration of products derived from starch into the processing process (starch is only a filler, there is no direct bond between synthetic polymer and starch) or, alternatively, the integration of products derived from starch into the production of polymers (starch and polymer form a stable bond).

The use of the starch as a pure filler cannot compete with other substances such as talcum. This situation is different when the specific starch properties become effective and the property profile of the end products is thus clearly changed. One example is the use of starch products in the processing of thermoplastic materials, such as polyethylene. Thereby, starch and the synthetic polymer are combined in a ratio of 1:1 by means of coexpression to form a 'master batch', from which various products are produced by means of common techniques using granulated polyethylene. The integration of starch in polyethylene films may cause an increased substance permeability in hollow bodies, improved water vapor permeability, improved antistatic behavior, improved antiblock behavior as well as improved printability with aqueous dyes.

Another possibility is the use of the starch in polyurethane foams. Due to the adaptation of starch derivatives as well as due to the optimization of processing techniques, it is possible to specifically control the reaction between synthetic polymers and the starch's hydroxy groups. The results are polyurethane films having the following property profiles due to the use of starch: a reduced coefficient of thermal expansion, decreased shrinking behavior, improved pressure/tension behavior, increased water vapor permeability without a change in water acceptance, reduced flammability and cracking density, no drop off of combustible parts, no halides and reduced aging. Disadvantages that presently still exist are reduced pressure and impact strength.

Product development of film is not the only option. Also solid plastics products, such as pots, plates and bowls can be produced by means of a starch content of more than 50%.

Furthermore, the starch/polymer mixtures offer the advantage that they are much easier biodegradable. Furthermore, due to their extreme capability to bind water, starch graft polymers have gained utmost importance. These are products having a backbone of starch and a side lattice of a synthetic monomer grafted on according to the principle of radical chain mechanism. The starch graft polymers available nowadays are characterized by an improved binding and retaining capability of up to 1000 g water per g starch at a high viscosity. These super absorbers are used mainly in the hygiene field, e.g. in products such as diapers and sheets, as well as in the agricultural sector, e.g. in seed pellets.

What is decisive for the use of the new starch modified by recombinant DNA techniques are, on the one hand, structure, water content, protein content, lipid content, fiber content, ashes/phosphate content, amylose/amylopectin ratio, distribution of the relative molar mass, degree of branching, granule size and shape as well as crystallization, and on the other hand, the properties resulting in the following features: flow and sorption behavior, pastification temperature, viscosity, thickening performance, solubility, paste structure, transparency, heat, shear and acid resistance, tendency to retrogradiation, capability of gel formation, resistance to freezing/thawing, capability of complex formation, iodine binding, film formation, adhesive strength, enzyme stability, digestibility and reactivity. The most remarkable feature is viscosity.

Moreover, the modified starch obtained from the plant cells of the invention may be subjected to further chemical modification, which will result in further improvement of the quality for certain of the above-described fields of application. These chemical modifications are principally known to the person skilled in the art. These are particularly modifications by means of acid treatment oxidation and esterification (formation of phosphate, nitrate, sulphate, xanthate, acetate and citrate starches. Further organic acids may also be used for esterification.)

formation of starch ethers (starch alkyl ether, O-allyl ether, hydroxylalkyl ether, O-carboxylmethyl ether, N-containing starch ethers, S-containing starch ethers)

formation of branched starches formation of starch graft polymers.

The invention also relates to propagation material of the plants of the invention, such as seeds, fruits, cuttings, tubers or root stocks, wherein this propagation material contains plant cells of the invention.

Plasmid pOs_R1 described in the present invention was deposited in accordance with the requirements of the Budapest Treaty at the Deutsche Sammlung fur Mikroorganismen und Zellkulturen (DSMZ), Mascheroder Weg 1b D-38124, Braunschweig, Federal Republic of Germany on Oct. 1, 1998, under accession number DSM 12439.

FIG. 1 shows schematically the structure of the plasmid pcoOs_R1.

A: CaMV 35S termination signal (Topfer et al., *Nucleic Acids Res.* 15 (1987), 5890)

B: *pat* gene

C: CaMV 35S promoter (Odell et al, *Nature* 313 (1985), 180)

D: Ubiquitin promoter (Toki et al., *Plant Phys.*100 (1992), 1503-1507)

E: Ubiquitin intron (Christensen et al., *Plant. Mol. Biol.* 18 (1992), 675-689)

F: SmaI/SnaBI-fragment of pOs_R1 (4427 bp)

G: nos terminator (Depicker et al., *J. Appl. Genet.* 1 (1982) 561-573)

LB: T-DNA left border

RB: T-DNA right border

The following Examples illustrate the invention.

EXAMPLE 1

Cloning of a cDNA from *Oryza sativa* Encoding an R1 Enzyme

Total RNA derived from green parts of 8 week old rice plants (indica variety IR36) was prepared according to published procedures (Logemann et al., *Anal. Biochem.* 163 (1987), 21-26). 1 mg of total RNA was used as a source to prepare poly A+ RNA, using the Oligotex mRNA purification Kit (Qiagen) according to the manufacturer's manual. 5 µg poly A+ RNA was used to construct a cDNA library, following manufacturer's manual (ZAP cDNA Synthesis Kit [Stratagene]).

The average size of cDNA inserts in the recombinant phages was 1.3 kb. Plaque lifting was performed on about $2\times10^5$ recombinant phages of the non-amplified library, using Hybond N filters (Amersham).

After pre-hybridization for 4 h at 42° C. in buffer A (5×SSC, 0.5% BSA, 5×Denhardt, 1% SDS, 40 mM phosphate buffer, pH 7.2, 100 mg/l herring sperm DNA, 25% formamid) filters were hybridized to the radiolabeled (Random Primed DNA Labeling Kit) 947 bp EcoRI/XhoI fragment of the R1 cDNA from maize (WO 98/27212). After 8 h of hybridization at 42° C. the filters were washed 3 times for 20 min at 50° C. in a buffer containing 3×SSC, 0.5% SDS. X-ray film exposure was usually performed for 14h.

Phage plaques which strongly hybridized were rescreened and purified. Plasmids were isolated by *in vivo excision*, according to the manufacturer's manual and characterized by restriction mapping. DNA sequence analysis was performed on plasmids containing the longest cDNA insertions. One of them, designated as pOs_R1 contained the nucleotide sequence information shown in Seq. ID No. 2.

The cDNA is only partial insofar as part of the 5'-end is missing. However, the missing 5'-end can be isolated by methods well known in the art, such as the 5'-RACE (rapid amplification of cDNA ends) method. With this method it is possible to amplify a missing 5'-end of a cDNA by making use of a polymerase chain reaction. This method may be carried out with the "Marathon cDNA amplification kit" of Clontech. Other possibilities for cloning the missing 5'-end are other PCR reactions, e.g. by using a λgt11 rice cDNA library (Clontech, Palo Alto, Calif., USA), carrying out an immunoscreen or by using standard hybridization methods as described, for example, in Sambrook et al., *Molecular Cloning, A Laboratory Manual*, $2^{nd}$ edition (1989) Cold Spring Harbor Laboratory Press, Cold Spring Harbor, N.Y.

EXAMPLE 2

Construct for Cosuppression of the R1 Gene in Rice

In order to be able to produce rice plants with a reduced amount of the protein encoded by the cDNA described in Example 1, a plasmid was constructed which allows to achieve a cosuppression effect in plant cells. This plasmid, which can be used for the transformation of plant cells comprises the following sequences:

- the 35S promoter of the CaMV (Odell et al., *Nature* 313 (1985), 180);
- the 35S termination sequence (Topfer et al., *Nucl. Acids Res.* 15 (1987), 5890);
- the pat gene as a selection marker;
- the ubiquitin promoter (Toki et al., *Plant Physiol.* 100 (1992), 1503-1507);
- the ubiquitin intron (Christensen et al., *Plant Mol. Biol.* 18 (1992), 675-689);
- the SmaI/SnaBI-fragment of the plasmid pOS_R1 containing the cDNA described in Example 1 (4427 bp);
- the nos terminator (Depicker et al., *J. Appl. Genet.* 1 (1982), 561-573); and
- the T-DNA left and right border sequences.

The structure of the plasmid, which was designated pcoOs_R1, is shown in FIG. 1. This plasmid is used to transform rice plant cells, e.g., by Agrobacterium-mediated gene transfer or by particle bombardment, and to regenerate transformed rice plants.

What is claimed:

1. An isolated nucleic acid molecule comprising a promoter operably linked to a nucleic acid in antisense orientation thereto, wherein the nucleic acid comprises
   (a) nucleotides 2 to 4372 of SEQ ID NO: 1;
   (b) the coding region of the cDNA insert of plasmid pOs R1, a sample of which has been deposited as DSMZ deposit accession number DSM 12439; or
   (c) a nucleic acid sequence that is at least 95% identical to the nucleic acid sequence of nucleotides 2 to 4372 of SEQ ID NO: 1 or the coding region of the cDNA insert of plasmid pOs R1, a sample of which has been deposited as DSMZ deposit accession number DSM 12439;
   wherein the nucleic acid sequence is sufficient to reduce the expression of a gene encoding an R1 protein in a rice cell when introduced in antisense orientation with respect to the promoter.

2. The nucleic acid molecule according to claim 1, wherein said nucleic acid comprises
   (a) a nucleic acid sequence encoding the amino add sequence of SEQ ID NO: 2; or
   (b) a nucleic acid sequence encoding the amino acid sequence encoded by the cDNA insert of plasmid pOs R1, a sample of which has been deposited as DSMZ deposit accession number DSM 12439.

3. The isolated nucleic acid molecule of claim 1, wherein the nucleic acid comprises the nucleotides 2 to 4372 of SEQ ID NO:1.

4. The isolated nucleic acid molecule of claim 1, wherein the nucleic acid comprises the coding region of the cDNA insert of plasmid pOs R1, a sample of which has been deposited as DSMZ deposit accession number DSM 12439.

5. The isolated nucleic acid molecule of claim 1, wherein the nucleic acid comprises a nucleic acid sequence that is at least 95% identical to the nucleic acid sequence of or the coding region of the cDNA insert of plasmid pOs R1, a sample of which has been deposited as DSMZ deposit accession number DSM 12439.

6. The isolated nucleic acid molecule of claim 2, wherein the nucleic acid comprises a nucleic acid sequence encoding the amino acid sequence of SEQ ID NO: 2.

7. The isolated nucleic add molecule of claim 2, wherein the nucleic acid comprises a nucleic acid sequence encoding the amino acid sequence encoded by the cDNA insert of plasmid pOs R1, a sample of which has been deposited as DSMZ deposit accession number DSM 12439.

8. An isolated nucleic acid molecule comprising a promoter operably linked to a nucleic acid sequence in antisense orientation thereto, wherein the nucleic add sequence comprises nucleotides 2 to 4372 of SEQ ID NO: 1, and wherein the nucleic acid sequence is sufficient to reduce the expression of a gene encoding an R1 protein an a rice cell when introduced in an antisense orientation with respect to the promoter.

9. A vector comprising the nucleic acid molecule according to any one of claims 1,2, or 3-7.

10. A host cell genetically modified with the nucleic acid molecule according to any one of claims 1,2, 8, or 3-7, or with a vector comprising said nucleic acid molecule.

11. The host cell according to claim 10, wherein the host cell is a plant cell.

12. A plant comprising the host cell according to claim 11.

13. The plant according to claim 12, wherein the plant is a starch-storing plant.

14. The plant according to claim 13, wherein the plant is rye, barley, wheat, rice, maize, pea, cassava or potato.

15. The plant according to claim 14, wherein the plant is a rice plant.

16. A propagation material comprising the host cell according to claim 11.

17. A method for producing a rice plant cell that synthesizes a modified starch, said method comprising the steps of introducing the nucleic acid molecule according to claim 1 into a rice plant cell such that said nucleic acid molecule is expressed, wherein expression of said nucleic acid molecule leads to the reduction of the expression of a gene encoding an R1 protein in the rice plant cell due to an antisense effect, wherein said rice plant cell synthesizes a modified starch.

18. A rice plant cell obtainable by the method according to claim 17.

19. A rice plant comprising the rice plant cell according to claim 18.

20. A propagation material comprising the rice plant cell according to claim 18.

* * * * *

SEQUENCE LISTING

```
<160> NUMBER OF SEQ ID NOS: 26

<210> SEQ ID NO 1
<211> LENGTH: 4643
<212> TYPE: DNA
<213> ORGANISM: Oryza sativa
<220> FEATURE:
<221> NAME/KEY: CDS
<222> LOCATION: (2)..(4375)

<400> SEQUENCE: 1 g aat tcg gca cga gcc gcg gca gct gct gcg gcc gag cgg tgc gcg ctc      49
  Asn Ser Ala Arg Ala Ala Ala Ala Ala Ala Glu Arg Cys Ala Leu
  1               5                  10                  15 ggc ctc ggc gtc cac gcg cgc ccc gcc tcg ccc tcg ccg gcg ctg ctc      97
Gly Leu Gly Val His Ala Arg Pro Ala Ser Pro Ser Pro Ala Leu Leu
            20                  25                  30 ccg ccg gcg gct ctc cgc cgc ggc cgc cgc ctc ccc gcg gcc acc acc     145
Pro Pro Ala Ala Leu Arg Arg Gly Arg Arg Leu Pro Ala Ala Thr Thr
        35                  40                  45 acc ctc gcc gtc tcc cgt cgg agc ctc ctc gcc cct cgc gcc atc gcc     193
Thr Leu Ala Val Ser Arg Arg Ser Leu Leu Ala Pro Arg Ala Ile Ala
    50                  55                  60 gct tcc acc ggc cgc gcc tcc ccg ggc ctt gtc gga agg ttc acc ctg     241
Ala Ser Thr Gly Arg Ala Ser Pro Gly Leu Val Gly Arg Phe Thr Leu
65                  70                  75                  80 gat gcc aac tcc gag ctt aag gtg aca ttg aac cca gca ccg cag ggt     289
Asp Ala Asn Ser Glu Leu Lys Val Thr Leu Asn Pro Ala Pro Gln Gly
                85                  90                  95 tcg gtg gcg gag atc aat cta gag gca act aac acc agc ggc tcc ctg     337
```

-continued

```
               Ser Val Ala Glu Ile Asn Leu Glu Ala Thr Asn Thr Ser Gly Ser Leu
                              100                 105                 110 ata ctg cat tgg ggc gcc ctt cgc ccg gat aga gga gaa tgg ctc cta      385
Ile Leu His Trp Gly Ala Leu Arg Pro Asp Arg Gly Glu Trp Leu Leu
            115                 120                 125 cca tcc cgg aaa cca gat ggc acg aca gtg tac aag aac agg gct ctt      433
Pro Ser Arg Lys Pro Asp Gly Thr Thr Val Tyr Lys Asn Arg Ala Leu
        130                 135                 140 agg acg cct ttt ata aag tca ggt gat aac tcc acg ctg aaa att gag      481
Arg Thr Pro Phe Ile Lys Ser Gly Asp Asn Ser Thr Leu Lys Ile Glu
145                 150                 155                 160 ata gat gat cct gca gtg caa gcc att gag ttc ctc ata ttt gat gag      529
Ile Asp Asp Pro Ala Val Gln Ala Ile Glu Phe Leu Ile Phe Asp Glu
                165                 170                 175 gca cgg aat aat tgg tac aaa aac aat ggc cag aat ttc caa att cag      577
Ala Arg Asn Asn Trp Tyr Lys Asn Asn Gly Gln Asn Phe Gln Ile Gln
            180                 185                 190 cta caa gcg agc caa tat caa ggg cag ggt aca tct act gct act tct      625
Leu Gln Ala Ser Gln Tyr Gln Gly Gln Gly Thr Ser Thr Ala Thr Ser
        195                 200                 205 tct act gtg gtt cca gag gat ctt gtg cag ata caa tca tat ctt cgg      673
Ser Thr Val Val Pro Glu Asp Leu Val Gln Ile Gln Ser Tyr Leu Arg
210                 215                 220 tgg gaa aga aag gga aag cag tca tat aca cct gag caa gag aag gag      721
Trp Glu Arg Lys Gly Lys Gln Ser Tyr Thr Pro Glu Gln Glu Lys Glu
225                 230                 235                 240 gag tat gaa gca gca cga act gag ttg ata gag gaa tta aac aag ggt      769
Glu Tyr Glu Ala Ala Arg Thr Glu Leu Ile Glu Glu Leu Asn Lys Gly
                245                 250                 255 gtt tct ttg gag aag cta cga gcg aaa ctg aca aag aca cct gag gca      817
Val Ser Leu Glu Lys Leu Arg Ala Lys Leu Thr Lys Thr Pro Glu Ala
            260                 265                 270 act gat agt aat gct cct gca tct gaa agc act gtg act act aaa gtc      865
Thr Asp Ser Asn Ala Pro Ala Ser Glu Ser Thr Val Thr Thr Lys Val
        275                 280                 285 cca gag gaa ctt gta caa gtc cag gct tac ata agg tgg gag aaa gca      913
Pro Glu Glu Leu Val Gln Val Gln Ala Tyr Ile Arg Trp Glu Lys Ala
    290                 295                 300 ggc aag cca aat tat gcc cca gag aag caa ttg gtc gag ttt gag gaa      961
Gly Lys Pro Asn Tyr Ala Pro Glu Lys Gln Leu Val Glu Phe Glu Glu
305                 310                 315                 320 gca agg aag gaa ctg cag tct gag ttg gat aag ggg acc tca gtt gag     1009
Ala Arg Lys Glu Leu Gln Ser Glu Leu Asp Lys Gly Thr Ser Val Glu
                325                 330                 335 cag ttg agg aac aaa att ttg aaa ggg aac att gag aca aaa gtt tcc     1057
Gln Leu Arg Asn Lys Ile Leu Lys Gly Asn Ile Glu Thr Lys Val Ser
            340                 345                 350 aag cag ctg aag gac aaa aaa tac ttt tct gtg gaa aga att cag cgg     1105
Lys Gln Leu Lys Asp Lys Lys Tyr Phe Ser Val Glu Arg Ile Gln Arg
        355                 360                 365 aaa aaa cga gat att gtg caa cta ctt aaa aaa cac aag cct act gtt     1153
Lys Lys Arg Asp Ile Val Gln Leu Leu Lys Lys His Lys Pro Thr Val
370                 375                 380 atg gaa gcg caa gca gag act cct aaa caa ccc act gtt ctg gat ctc     1201
Met Glu Ala Gln Ala Glu Thr Pro Lys Gln Pro Thr Val Leu Asp Leu
385                 390                 395                 400 ttc aca aag tca tta cag gag cag gat aac tgt gag gtt cta agc aga     1249
Phe Thr Lys Ser Leu Gln Glu Gln Asp Asn Cys Glu Val Leu Ser Arg
                405                 410                 415
```

```
                                       -continued
aag ctt ttc aag ttc ggt gac aag gag ata ctg gga att acc acc gtt    1297
Lys Leu Phe Lys Phe Gly Asp Lys Glu Ile Leu Gly Ile Thr Thr Val
        420                 425                 430 gct cta gga aaa acc aaa gtt cac ttg gca aca aac tat atg gag cca    1345
Ala Leu Gly Lys Thr Lys Val His Leu Ala Thr Asn Tyr Met Glu Pro
            435                 440                 445 ctt ata ctt cac tgg gcg ttg tca aaa gag aat gga gag tgg cag gca    1393
Leu Ile Leu His Trp Ala Leu Ser Lys Glu Asn Gly Glu Trp Gln Ala
    450                 455                 460 cct ccc tca agc ata ttg cca tct ggt tca tca ttg cta gac aag gca    1441
Pro Pro Ser Ser Ile Leu Pro Ser Gly Ser Ser Leu Leu Asp Lys Ala
465                 470                 475                 480 tgt gaa act tca ttc agt gaa tat gaa ttg aat ggt ctg cat tgt cag    1489
Cys Glu Thr Ser Phe Ser Glu Tyr Glu Leu Asn Gly Leu His Cys Gln
                485                 490                 495 gtt gtt gag atc gag ctt gac gat ggt gga tac aag cgg atg ccc ttt    1537
Val Val Glu Ile Glu Leu Asp Asp Gly Gly Tyr Lys Arg Met Pro Phe
            500                 505                 510 gtt ctc cgg tct ggt gaa aca tgg atg aaa aat aat ggc tct gac ttt    1585
Val Leu Arg Ser Gly Glu Thr Trp Met Lys Asn Asn Gly Ser Asp Phe
        515                 520                 525 tac ttg gat ttc agc acc aaa gtt gca aaa aat aca aag gat act ggt    1633
Tyr Leu Asp Phe Ser Thr Lys Val Ala Lys Asn Thr Lys Asp Thr Gly
    530                 535                 540 gat gct ggt aaa ggc act gct aag gcc ttg ctt gaa aga ata gca gat    1681
Asp Ala Gly Lys Gly Thr Ala Lys Ala Leu Leu Glu Arg Ile Ala Asp
545                 550                 555                 560 cta gag gaa gat gcc caa cga tct ctt atg cac aga ttc aat att gca    1729
Leu Glu Glu Asp Ala Gln Arg Ser Leu Met His Arg Phe Asn Ile Ala
                565                 570                 575 gca gat cta gtt gac caa gca aga gat aat gga tta ttg ggt att att    1777
Ala Asp Leu Val Asp Gln Ala Arg Asp Asn Gly Leu Leu Gly Ile Ile
            580                 585                 590 gga att ttt gtt tgg att agg ttc atg gct aca agg caa cta ata tgg    1825
Gly Ile Phe Val Trp Ile Arg Phe Met Ala Thr Arg Gln Leu Ile Trp
        595                 600                 605 aac aag aac tac aat gtg aag cca cgt gag ata agc aaa gca caa gat    1873
Asn Lys Asn Tyr Asn Val Lys Pro Arg Glu Ile Ser Lys Ala Gln Asp
    610                 615                 620 agg ttt aca gat gat ctt gag aat atg tac aga act tac cca caa tat    1921
Arg Phe Thr Asp Asp Leu Glu Asn Met Tyr Arg Thr Tyr Pro Gln Tyr
625                 630                 635                 640 cag gag atc tta aga atg ata atg tct gct gtt ggt cgg gga ggt gaa    1969
Gln Glu Ile Leu Arg Met Ile Met Ser Ala Val Gly Arg Gly Gly Glu
                645                 650                 655 ggt gat gtt ggt caa cgc att cgt gat gag ata tta gta atc cag aga    2017
Gly Asp Val Gly Gln Arg Ile Arg Asp Glu Ile Leu Val Ile Gln Arg
            660                 665                 670 aat aat gac tgc aaa ggt gga atg atg gag gag tgg cac cag aaa ctg    2065
Asn Asn Asp Cys Lys Gly Gly Met Met Glu Glu Trp His Gln Lys Leu
        675                 680                 685 cac aac aat aca agc cca gat gat gta gtg atc tgc cag gcc cta ctt    2113
His Asn Asn Thr Ser Pro Asp Asp Val Val Ile Cys Gln Ala Leu Leu
    690                 695                 700 gat tat atc aag agt gat ttt gat att ggt gtt tac tgg gac acc ttg    2161
Asp Tyr Ile Lys Ser Asp Phe Asp Ile Gly Val Tyr Trp Asp Thr Leu
705                 710                 715                 720 aaa aaa gat ggt ata aca aaa gag cgt cta ttg agc tat gat cga ccg    2209
Lys Lys Asp Gly Ile Thr Lys Glu Arg Leu Leu Ser Tyr Asp Arg Pro
                725                 730                 735
```

```
att cat tca gag cca aat ttc agg agt gaa cag aaa gat ggc tta ctc      2257
Ile His Ser Glu Pro Asn Phe Arg Ser Glu Gln Lys Asp Gly Leu Leu
        740                 745                 750 cgt gac ttg ggc aat tat atg aga agc ctc aag gca gtg cat tct ggt      2305
Arg Asp Leu Gly Asn Tyr Met Arg Ser Leu Lys Ala Val His Ser Gly
755                 760                 765 gct gat ctt gaa tct gct ata gca act tgc atg gga tac aaa tca gag      2353
Ala Asp Leu Glu Ser Ala Ile Ala Thr Cys Met Gly Tyr Lys Ser Glu
        770                 775                 780 ggt gaa ggt ttc atg gtt ggt gtt cag att aat cca gtg aag ggt ttg      2401
Gly Glu Gly Phe Met Val Gly Val Gln Ile Asn Pro Val Lys Gly Leu
785                 790                 795                 800 cca tct gga ttt cct aaa ttg ctt gaa ttt gta ctt gac cat gtt gag      2449
Pro Ser Gly Phe Pro Lys Leu Leu Glu Phe Val Leu Asp His Val Glu
                805                 810                 815 gat aaa tca gca gaa cca ctt ctt gag ggg tta ttg gag gct cga gct      2497
Asp Lys Ser Ala Glu Pro Leu Leu Glu Gly Leu Leu Glu Ala Arg Ala
            820                 825                 830 gaa cta cac cct ttg ctc ctt ggc tct cct gaa cgc atg aag gat ctt      2545
Glu Leu His Pro Leu Leu Leu Gly Ser Pro Glu Arg Met Lys Asp Leu
        835                 840                 845 atc ttt tta gac att gct ctt gat tct act ttc agg aca gca gtt gaa      2593
Ile Phe Leu Asp Ile Ala Leu Asp Ser Thr Phe Arg Thr Ala Val Glu
850                 855                 860 aga tca tat gag gag ctc aat aat gta gaa cca gag aaa att atg tac      2641
Arg Ser Tyr Glu Glu Leu Asn Asn Val Glu Pro Glu Lys Ile Met Tyr
865                 870                 875                 880 ttc atc agt ctt gtc ctt gaa aat ctt gct tta tcc acc gac gac aat      2689
Phe Ile Ser Leu Val Leu Glu Asn Leu Ala Leu Ser Thr Asp Asp Asn
                885                 890                 895 gaa gat atc cta tat tgc tta aag gga tgg aat caa gcc ttg gaa atg      2737
Glu Asp Ile Leu Tyr Cys Leu Lys Gly Trp Asn Gln Ala Leu Glu Met
            900                 905                 910 gct aaa cag aaa aac aac caa tgg gct ctc tat gct aaa gca ttt ctg      2785
Ala Lys Gln Lys Asn Asn Gln Trp Ala Leu Tyr Ala Lys Ala Phe Leu
        915                 920                 925 gac aga acc aga ctt gcc ctt gca agc aag gga gaa caa tac tat aat      2833
Asp Arg Thr Arg Leu Ala Leu Ala Ser Lys Gly Glu Gln Tyr Tyr Asn
930                 935                 940 ttg atg cag ccc tca gct gaa tat ctt ggc tcg tta ctt aac att gac      2881
Leu Met Gln Pro Ser Ala Glu Tyr Leu Gly Ser Leu Leu Asn Ile Asp
945                 950                 955                 960 caa tgg gca gtt aat atc ttt aca gaa gaa att att cgt ggt gga tca      2929
Gln Trp Ala Val Asn Ile Phe Thr Glu Glu Ile Ile Arg Gly Gly Ser
                965                 970                 975 gct gct acc ctg tct gct ctt ctg aat cgg att gat cct gtt ctt agg      2977
Ala Ala Thr Leu Ser Ala Leu Leu Asn Arg Ile Asp Pro Val Leu Arg
            980                 985                 990 aat gtt gca cag ctt gga agt tgg cag gtt ata agc cca gtt gaa gta      3025
Asn Val Ala Gln Leu Gly Ser Trp Gln Val Ile Ser Pro Val Glu Val
        995                 1000                1005 tca ggt tac att gta gtg gtt gat gaa ttg ctt gct gtt caa aac aaa      3073
Ser Gly Tyr Ile Val Val Val Asp Glu Leu Leu Ala Val Gln Asn Lys
   1010                1015                1020 tcc tat gat aaa cca act atc ctt gtg gca aag agt gtc aag gga gag      3121
Ser Tyr Asp Lys Pro Thr Ile Leu Val Ala Lys Ser Val Lys Gly Glu
 1025                1030                1035                1040 gaa gaa ata cca gat gga gtt gtt ggt gtt att aca cct gat atg cca      3169
Glu Glu Ile Pro Asp Gly Val Val Gly Val Ile Thr Pro Asp Met Pro
```

-continued

```
                1045                1050               1055
gat gtt ctc tcc cat gta tca gtc cga gca agg aat tgc aag gtt tta    3217
Asp Val Leu Ser His Val Ser Val Arg Ala Arg Asn Cys Lys Val Leu
        1060                1065                1070 ttt gca aca tgc ttt gat cct aac acc ttg tct gaa ctc caa gga cat    3265
Phe Ala Thr Cys Phe Asp Pro Asn Thr Leu Ser Glu Leu Gln Gly His
        1075                1080                1085 gat ggg aaa gtg ttt tcc ttc aaa cct act tct gca gat atc acc tat    3313
Asp Gly Lys Val Phe Ser Phe Lys Pro Thr Ser Ala Asp Ile Thr Tyr
        1090                1095                1100 agg gag att cca gag agt gaa ctg caa tca ggt tct cta aat gca gaa    3361
Arg Glu Ile Pro Glu Ser Glu Leu Gln Ser Gly Ser Leu Asn Ala Glu
1105                1110                1115                1120 gct ggc cag gca gtg cca tct gtg tca tta gtc aag aag aag ttt ctt    3409
Ala Gly Gln Ala Val Pro Ser Val Ser Leu Val Lys Lys Lys Phe Leu
        1125                1130                1135 gga aaa tat gca ata tca gca gaa gaa ttc tct gag gaa atg gtt ggg    3457
Gly Lys Tyr Ala Ile Ser Ala Glu Glu Phe Ser Glu Glu Met Val Gly
        1140                1145                1150 gcc aag tct cgc aac gta gca tac ctc aaa gga aaa gta ccc tca tgg    3505
Ala Lys Ser Arg Asn Val Ala Tyr Leu Lys Gly Lys Val Pro Ser Trp
        1155                1160                1165 gtt ggt gtc cct aca tca gtt gcg att cca ttt ggg acc ttt gag aag    3553
Val Gly Val Pro Thr Ser Val Ala Ile Pro Phe Gly Thr Phe Glu Lys
        1170                1175                1180 gtt ttg tct gat gaa atc aat aag gaa gtc gcg caa acc ata caa atg    3601
Val Leu Ser Asp Glu Ile Asn Lys Glu Val Ala Gln Thr Ile Gln Met
1185                1190                1195                1200 ctg aag gga aaa ctt gct caa gat gat ttt agt gct cta ggc gaa ata    3649
Leu Lys Gly Lys Leu Ala Gln Asp Asp Phe Ser Ala Leu Gly Glu Ile
        1205                1210                1215 cgg aaa act gtt ctc aat tta act gct cct act caa ctg atc aag gaa    3697
Arg Lys Thr Val Leu Asn Leu Thr Ala Pro Thr Gln Leu Ile Lys Glu
        1220                1225                1230 ctg aag gag aag atg cta ggc tct gga atg ccc tgg cct gga gat gaa    3745
Leu Lys Glu Lys Met Leu Gly Ser Gly Met Pro Trp Pro Gly Asp Glu
        1235                1240                1245 ggt gac caa cgt tgg gag caa gca tgg atg gca att aaa aag gtt tgg    3793
Gly Asp Gln Arg Trp Glu Gln Ala Trp Met Ala Ile Lys Lys Val Trp
        1250                1255                1260 gcg tca aaa tgg aat gaa aga gca tat ttt agc act cgt aag gtg aag    3841
Ala Ser Lys Trp Asn Glu Arg Ala Tyr Phe Ser Thr Arg Lys Val Lys
1265                1270                1275                1280 ctt gat cat gac tac ctt tcc atg gct gta ctt gta caa gaa att gtc    3889
Leu Asp His Asp Tyr Leu Ser Met Ala Val Leu Val Gln Glu Ile Val
        1285                1290                1295 aac gca gac tat gcc ttt gtc att cat act act aac cca tca tcg gga    3937
Asn Ala Asp Tyr Ala Phe Val Ile His Thr Thr Asn Pro Ser Ser Gly
        1300                1305                1310 gat tcg tct gag ata tat gct gaa gtg gtg aaa ggg ctt gga gaa aca    3985
Asp Ser Ser Glu Ile Tyr Ala Glu Val Val Lys Gly Leu Gly Glu Thr
        1315                1320                1325 ctt gta gga gcc tat cct ggt cgc gcc atg agc ttt gta tgt aag aaa    4033
Leu Val Gly Ala Tyr Pro Gly Arg Ala Met Ser Phe Val Cys Lys Lys
        1330                1335                1340 aac gac ctt gat tct ccc aag gta ctg ggt ttc cca agc aag cca att    4081
Asn Asp Leu Asp Ser Pro Lys Val Leu Gly Phe Pro Ser Lys Pro Ile
1345                1350                1355                1360 ggt ctc ttc ata aag aga tca atc atc ttt cgt tca gat tcc aac ggt    4129
```

```
Gly Leu Phe Ile Lys Arg Ser Ile Ile Phe Arg Ser Asp Ser Asn Gly
            1365                1370                1375 gag gat tta gaa ggg tat gct gga gca gga ctg tat gat agt gtc cct    4177
Glu Asp Leu Glu Gly Tyr Ala Gly Ala Gly Leu Tyr Asp Ser Val Pro
        1380                1385                1390 atg gat gag gaa gat gaa gtc ata ctc gac tac acc acc gac ccc ctc    4225
Met Asp Glu Glu Asp Glu Val Ile Leu Asp Tyr Thr Thr Asp Pro Leu
    1395                1400                1405 att aca gat cag gga ttc caa aaa tct atc ctc tcg agc att gca cgg    4273
Ile Thr Asp Gln Gly Phe Gln Lys Ser Ile Leu Ser Ser Ile Ala Arg
    1410                1415                1420 gct ggt cat gcc att gag gag ctt tat ggg tcc cca cag gat gtt gag    4321
Ala Gly His Ala Ile Glu Glu Leu Tyr Gly Ser Pro Gln Asp Val Glu
1425                1430                1435                1440 ggt gca gtg aag gaa ggg aag cta tac gta gta cag aca aga cca cag    4369
Gly Ala Val Lys Glu Gly Lys Leu Tyr Val Val Gln Thr Arg Pro Gln
                1445                1450                1455 atg taa tctatatgta tattttatag ccaagtcaat caggcaatgt tgtagagtaa     4425
Met gatatacggg ccgtgggaca tgtataacac gttacgccct ttttttatt atttgctttc   4485 atactcacaa tacactaatt tatagggctt attttatcgc caataagtgt aatctgacta   4545
tgatcataaa taagcctcct aggctactga aaaccattaa aggttatttt gatcaaaaaa   4605
aaaaaaaaaa aaaaaaaaa aaaaaaaaaa aactcgag                          4643

<210> SEQ ID NO 2
<211> LENGTH: 1457
<212> TYPE: PRT
<213> ORGANISM: Oryza sativa

<400> SEQUENCE: 2

Asn Ser Ala Arg Ala Ala Ala Ala Ala Glu Arg Cys Ala Leu
  1               5                  10                  15

Gly Leu Gly Val His Ala Arg Pro Ala Ser Pro Ser Pro Ala Leu Leu
                 20                  25                  30

Pro Pro Ala Ala Leu Arg Arg Gly Arg Leu Pro Ala Ala Thr Thr
             35                  40                  45

Thr Leu Ala Val Ser Arg Arg Ser Leu Leu Ala Pro Arg Ala Ile Ala
     50                  55                  60

Ala Ser Thr Gly Arg Ala Ser Pro Gly Leu Val Gly Arg Phe Thr Leu
 65                  70                  75                  80

Asp Ala Asn Ser Glu Leu Lys Val Thr Leu Asn Pro Ala Pro Gln Gly
                 85                  90                  95

Ser Val Ala Glu Ile Asn Leu Glu Ala Thr Asn Thr Ser Gly Ser Leu
                100                 105                 110

Ile Leu His Trp Gly Ala Leu Arg Pro Asp Arg Gly Glu Trp Leu Leu
            115                 120                 125

Pro Ser Arg Lys Pro Asp Gly Thr Thr Val Tyr Lys Asn Arg Ala Leu
        130                 135                 140

Arg Thr Pro Phe Ile Lys Ser Gly Asp Asn Ser Thr Leu Lys Ile Glu
145                 150                 155                 160

Ile Asp Asp Pro Ala Val Gln Ala Ile Glu Phe Leu Ile Phe Asp Glu
                165                 170                 175

Ala Arg Asn Asn Trp Tyr Lys Asn Asn Gly Gln Asn Phe Gln Ile Gln
            180                 185                 190

Leu Gln Ala Ser Gln Tyr Gln Gly Gln Gly Thr Ser Thr Ala Thr Ser
```

-continued

```
            195                 200                 205
Ser Thr Val Val Pro Glu Asp Leu Val Gln Ile Gln Ser Tyr Leu Arg
    210                 215                 220
Trp Glu Arg Lys Gly Lys Gln Ser Tyr Thr Pro Glu Gln Lys Glu
225                 230                 235                 240
Glu Tyr Glu Ala Ala Arg Thr Glu Leu Ile Glu Glu Leu Asn Lys Gly
                245                 250                 255
Val Ser Leu Glu Lys Leu Arg Ala Lys Leu Thr Lys Thr Pro Glu Ala
                260                 265                 270
Thr Asp Ser Asn Ala Pro Ala Ser Glu Ser Thr Val Thr Lys Val
        275                 280                 285
Pro Glu Glu Leu Val Gln Val Gln Ala Tyr Ile Arg Trp Glu Lys Ala
    290                 295                 300
Gly Lys Pro Asn Tyr Ala Pro Glu Lys Gln Leu Val Glu Phe Glu Glu
305                 310                 315                 320
Ala Arg Lys Glu Leu Gln Ser Glu Leu Asp Lys Gly Thr Ser Val Glu
                325                 330                 335
Gln Leu Arg Asn Lys Ile Leu Lys Gly Asn Ile Glu Thr Lys Val Ser
                340                 345                 350
Lys Gln Leu Lys Asp Lys Lys Tyr Phe Ser Val Glu Arg Ile Gln Arg
                355                 360                 365
Lys Lys Arg Asp Ile Val Gln Leu Leu Lys Lys His Lys Pro Thr Val
        370                 375                 380
Met Glu Ala Gln Ala Glu Thr Pro Lys Gln Pro Thr Val Leu Asp Leu
385                 390                 395                 400
Phe Thr Lys Ser Leu Gln Glu Gln Asp Asn Cys Glu Val Leu Ser Arg
                405                 410                 415
Lys Leu Phe Lys Phe Gly Asp Lys Glu Ile Leu Gly Ile Thr Thr Val
                420                 425                 430
Ala Leu Gly Lys Thr Lys Val His Leu Ala Thr Asn Tyr Met Glu Pro
            435                 440                 445
Leu Ile Leu His Trp Ala Leu Ser Lys Glu Asn Gly Glu Trp Gln Ala
        450                 455                 460
Pro Pro Ser Ser Ile Leu Pro Ser Gly Ser Ser Leu Leu Asp Lys Ala
465                 470                 475                 480
Cys Glu Thr Ser Phe Ser Glu Tyr Glu Leu Asn Gly Leu His Cys Gln
                485                 490                 495
Val Val Glu Ile Glu Leu Asp Asp Gly Gly Tyr Lys Arg Met Pro Phe
                500                 505                 510
Val Leu Arg Ser Gly Glu Thr Trp Met Lys Asn Asn Gly Ser Asp Phe
            515                 520                 525
Tyr Leu Asp Phe Ser Thr Lys Val Ala Lys Asn Thr Lys Asp Thr Gly
        530                 535                 540
Asp Ala Gly Lys Gly Thr Ala Lys Ala Leu Leu Glu Arg Ile Ala Asp
545                 550                 555                 560
Leu Glu Glu Asp Ala Gln Arg Ser Leu Met His Arg Phe Asn Ile Ala
                565                 570                 575
Ala Asp Leu Val Asp Gln Ala Arg Asp Asn Gly Leu Leu Gly Ile Ile
            580                 585                 590
Gly Ile Phe Val Trp Ile Arg Phe Met Ala Thr Arg Gln Leu Ile Trp
        595                 600                 605
Asn Lys Asn Tyr Asn Val Lys Pro Arg Glu Ile Ser Lys Ala Gln Asp
    610                 615                 620
```

-continued

```
Arg Phe Thr Asp Asp Leu Glu Asn Met Tyr Arg Thr Tyr Pro Gln Tyr
625                 630                 635                 640

Gln Glu Ile Leu Arg Met Ile Met Ser Ala Val Gly Arg Gly Gly Glu
            645                 650                 655

Gly Asp Val Gly Gln Arg Ile Arg Asp Glu Ile Leu Val Ile Gln Arg
                660                 665                 670

Asn Asn Asp Cys Lys Gly Gly Met Met Glu Glu Trp His Gln Lys Leu
            675                 680                 685

His Asn Asn Thr Ser Pro Asp Asp Val Val Ile Cys Gln Ala Leu Leu
        690                 695                 700

Asp Tyr Ile Lys Ser Asp Phe Asp Ile Gly Val Tyr Trp Asp Thr Leu
705                 710                 715                 720

Lys Lys Asp Gly Ile Thr Lys Glu Arg Leu Ser Tyr Asp Arg Pro
                725                 730                 735

Ile His Ser Glu Pro Asn Phe Arg Ser Glu Lys Asp Gly Leu Leu
                740                 745                 750

Arg Asp Leu Gly Asn Tyr Met Arg Ser Leu Lys Ala Val His Ser Gly
            755                 760                 765

Ala Asp Leu Glu Ser Ala Ile Ala Thr Cys Met Gly Tyr Lys Ser Glu
770                 775                 780

Gly Glu Gly Phe Met Val Gly Val Gln Ile Asn Pro Val Lys Gly Leu
785                 790                 795                 800

Pro Ser Gly Phe Pro Lys Leu Leu Glu Phe Val Leu Asp His Val Glu
                805                 810                 815

Asp Lys Ser Ala Glu Pro Leu Leu Glu Gly Leu Leu Glu Ala Arg Ala
            820                 825                 830

Glu Leu His Pro Leu Leu Gly Ser Pro Glu Arg Met Lys Asp Leu
        835                 840                 845

Ile Phe Leu Asp Ile Ala Leu Asp Ser Thr Phe Arg Thr Ala Val Glu
850                 855                 860

Arg Ser Tyr Glu Glu Leu Asn Asn Val Glu Pro Glu Lys Ile Met Tyr
865                 870                 875                 880

Phe Ile Ser Leu Val Leu Glu Asn Leu Ala Leu Ser Thr Asp Asp Asn
            885                 890                 895

Glu Asp Ile Leu Tyr Cys Leu Lys Gly Trp Asn Gln Ala Leu Glu Met
                900                 905                 910

Ala Lys Gln Lys Asn Asn Gln Trp Ala Leu Tyr Ala Lys Ala Phe Leu
        915                 920                 925

Asp Arg Thr Arg Leu Ala Leu Ala Ser Lys Gly Glu Gln Tyr Tyr Asn
930                 935                 940

Leu Met Gln Pro Ser Ala Glu Tyr Leu Gly Ser Leu Leu Asn Ile Asp
945                 950                 955                 960

Gln Trp Ala Val Asn Ile Phe Thr Glu Glu Ile Ile Arg Gly Gly Ser
                965                 970                 975

Ala Ala Thr Leu Ser Ala Leu Leu Asn Arg Ile Asp Pro Val Leu Arg
            980                 985                 990

Asn Val Ala Gln Leu Gly Ser Trp Gln Val Ile Ser Pro Val Glu Val
        995                 1000                1005

Ser Gly Tyr Ile Val Val Asp Glu Leu Leu Ala Val Gln Asn Lys
    1010                1015                1020

Ser Tyr Asp Lys Pro Thr Ile Leu Val Ala Lys Ser Val Lys Gly Glu
1025                1030                1035                1040
```

-continued

```
Glu Glu Ile Pro Asp Gly Val Val Gly Val Ile Thr Pro Asp Met Pro
            1045                1050                1055

Asp Val Leu Ser His Val Ser Val Arg Ala Arg Asn Cys Lys Val Leu
        1060                1065                1070

Phe Ala Thr Cys Phe Asp Pro Asn Thr Leu Ser Glu Leu Gln Gly His
        1075                1080                1085

Asp Gly Lys Val Phe Ser Phe Lys Pro Thr Ser Ala Asp Ile Thr Tyr
        1090                1095                1100

Arg Glu Ile Pro Glu Ser Glu Leu Gln Ser Gly Ser Leu Asn Ala Glu
1105                1110                1115                1120

Ala Gly Gln Ala Val Pro Ser Val Ser Leu Val Lys Lys Lys Phe Leu
            1125                1130                1135

Gly Lys Tyr Ala Ile Ser Ala Glu Glu Phe Ser Glu Glu Met Val Gly
            1140                1145                1150

Ala Lys Ser Arg Asn Val Ala Tyr Leu Lys Gly Lys Val Pro Ser Trp
        1155                1160                1165

Val Gly Val Pro Thr Ser Val Ala Ile Pro Phe Gly Thr Phe Glu Lys
        1170                1175                1180

Val Leu Ser Asp Glu Ile Asn Lys Glu Val Ala Gln Thr Ile Gln Met
1185                1190                1195                1200

Leu Lys Gly Lys Leu Ala Gln Asp Asp Phe Ser Ala Leu Gly Glu Ile
            1205                1210                1215

Arg Lys Thr Val Leu Asn Leu Thr Ala Pro Thr Gln Leu Ile Lys Glu
            1220                1225                1230

Leu Lys Glu Lys Met Leu Gly Ser Gly Met Pro Trp Pro Gly Asp Glu
        1235                1240                1245

Gly Asp Gln Arg Trp Glu Gln Ala Trp Met Ala Ile Lys Lys Val Trp
        1250                1255                1260

Ala Ser Lys Trp Asn Glu Arg Ala Tyr Phe Ser Thr Arg Lys Val Lys
1265                1270                1275                1280

Leu Asp His Asp Tyr Leu Ser Met Ala Val Leu Val Gln Glu Ile Val
            1285                1290                1295

Asn Ala Asp Tyr Ala Phe Val Ile His Thr Thr Asn Pro Ser Ser Gly
            1300                1305                1310

Asp Ser Ser Glu Ile Tyr Ala Glu Val Val Lys Gly Leu Gly Glu Thr
        1315                1320                1325

Leu Val Gly Ala Tyr Pro Gly Arg Ala Met Ser Phe Val Cys Lys Lys
        1330                1335                1340

Asn Asp Leu Asp Ser Pro Lys Val Leu Gly Phe Pro Ser Lys Pro Ile
1345                1350                1355                1360

Gly Leu Phe Ile Lys Arg Ser Ile Ile Phe Arg Ser Asp Ser Asn Gly
            1365                1370                1375

Glu Asp Leu Glu Gly Tyr Ala Gly Ala Gly Leu Tyr Asp Ser Val Pro
            1380                1385                1390

Met Asp Glu Glu Asp Glu Val Ile Leu Asp Tyr Thr Thr Asp Pro Leu
        1395                1400                1405

Ile Thr Asp Gln Gly Phe Gln Lys Ser Ile Leu Ser Ser Ile Ala Arg
        1410                1415                1420

Ala Gly His Ala Ile Glu Glu Leu Tyr Gly Ser Pro Gln Asp Val Glu
1425                1430                1435                1440

Gly Ala Val Lys Glu Gly Lys Leu Tyr Val Val Gln Thr Arg Pro Gln
            1445                1450                1455

Met
```

<210> SEQ ID NO 3
<211> LENGTH: 5
<212> TYPE: PRT
<213> ORGANISM: Oryza sativa

<400> SEQUENCE: 3

Pro Phe Ile Lys Ser
 1               5

<210> SEQ ID NO 4
<211> LENGTH: 5
<212> TYPE: PRT
<213> ORGANISM: Oryza sativa

<400> SEQUENCE: 4

Gln Ala Ile Glu Phe
 1               5

<210> SEQ ID NO 5
<211> LENGTH: 5
<212> TYPE: PRT
<213> ORGANISM: Oryza sativa

<400> SEQUENCE: 5

Asn Tyr Ala Pro Glu
 1               5

<210> SEQ ID NO 6
<211> LENGTH: 5
<212> TYPE: PRT
<213> ORGANISM: Oryza sativa

<400> SEQUENCE: 6

Glu Leu Gln Ser Glu
 1               5

<210> SEQ ID NO 7
<211> LENGTH: 6
<212> TYPE: PRT
<213> ORGANISM: Oryza sativa

<400> SEQUENCE: 7

Lys Val Ala Lys Asn Thr
 1               5

<210> SEQ ID NO 8
<211> LENGTH: 5
<212> TYPE: PRT
<213> ORGANISM: Oryza sativa

<400> SEQUENCE: 8

Ala Ala Asp Leu Val
 1               5

<210> SEQ ID NO 9
<211> LENGTH: 5
<212> TYPE: PRT
<213> ORGANISM: Oryza sativa

<400> SEQUENCE: 9

Gln Tyr Gln Glu Ile
 1               5

```
<210> SEQ ID NO 10
<211> LENGTH: 5
<212> TYPE: PRT
<213> ORGANISM: Oryza sativa

<400> SEQUENCE: 10

Ala Leu Leu Asp Tyr
 1               5

<210> SEQ ID NO 11
<211> LENGTH: 5
<212> TYPE: PRT
<213> ORGANISM: Oryza sativa

<400> SEQUENCE: 11

Asp Arg Pro Ile His
 1               5

<210> SEQ ID NO 12
<211> LENGTH: 5
<212> TYPE: PRT
<213> ORGANISM: Oryza sativa

<400> SEQUENCE: 12

Gln Lys Asp Gly Leu
 1               5

<210> SEQ ID NO 13
<211> LENGTH: 5
<212> TYPE: PRT
<213> ORGANISM: Oryza sativa

<400> SEQUENCE: 13

Gln Lys Asp Gly Leu
 1               5

<210> SEQ ID NO 14
<211> LENGTH: 5
<212> TYPE: PRT
<213> ORGANISM: Oryza sativa

<400> SEQUENCE: 14

Ala Arg Ala Glu Leu
 1               5

<210> SEQ ID NO 15
<211> LENGTH: 5
<212> TYPE: PRT
<213> ORGANISM: Oryza sativa

<400> SEQUENCE: 15

Ala Leu Ser Thr Asp
 1               5

<210> SEQ ID NO 16
<211> LENGTH: 5
<212> TYPE: PRT
<213> ORGANISM: Oryza sativa

<400> SEQUENCE: 16

Asn Arg Ile Asp Pro
 1               5

<210> SEQ ID NO 17
<211> LENGTH: 5
```

```
<212> TYPE: PRT
<213> ORGANISM: Oryza sativa

<400> SEQUENCE: 17

Gly Tyr Ile Val Val
 1               5

<210> SEQ ID NO 18
<211> LENGTH: 5
<212> TYPE: PRT
<213> ORGANISM: Oryza sativa

<400> SEQUENCE: 18

Arg Asn Cys Lys Val
 1               5

<210> SEQ ID NO 19
<211> LENGTH: 5
<212> TYPE: PRT
<213> ORGANISM: Oryza sativa

<400> SEQUENCE: 19

Leu Gly Phe Pro Ser
 1               5

<210> SEQ ID NO 20
<211> LENGTH: 5
<212> TYPE: PRT
<213> ORGANISM: Oryza sativa

<400> SEQUENCE: 20

Val Ile Leu Asp Tyr
 1               5

<210> SEQ ID NO 21
<211> LENGTH: 5
<212> TYPE: PRT
<213> ORGANISM: Oryza sativa

<400> SEQUENCE: 21

Phe Gln Lys Ser Ile
 1               5

<210> SEQ ID NO 22
<211> LENGTH: 5
<212> TYPE: PRT
<213> ORGANISM: Oryza sativa

<400> SEQUENCE: 22

Glu Gly Ala Val Lys
 1               5

<210> SEQ ID NO 23
<211> LENGTH: 5
<212> TYPE: PRT
<213> ORGANISM: Oryza sativa

<400> SEQUENCE: 23

Val Lys Glu Gly Lys
 1               5

<210> SEQ ID NO 24
<211> LENGTH: 5
<212> TYPE: PRT
<213> ORGANISM: Oryza sativa
```

```
<400> SEQUENCE: 24

Lys Leu Tyr Val Val
1               5

<210> SEQ ID NO 25
<211> LENGTH: 27
<212> TYPE: DNA
<213> ORGANISM: Artificial Sequence
<220> FEATURE:
<223> OTHER INFORMATION: Description of Artificial Sequence: artificial

<400> SEQUENCE: 25
gagaccatgg tacttaccac tgatacc                                      27

<210> SEQ ID NO 26
<211> LENGTH: 18
<212> TYPE: DNA
<213> ORGANISM: Artificial Sequence
<220> FEATURE:
<223> OTHER INFORMATION: Description of Artificial Sequence: artificial

<400> SEQUENCE: 26
gtacttgtac tgcaggac                                                18
```